(12) United States Patent
Paarup Kylling et al.

(10) Patent No.: US 10,282,842 B2
(45) Date of Patent: May 7, 2019

(54) METHODS AND APPARATUS FOR ANALYSING EMBRYO DEVELOPMENT

(71) Applicant: Unisense FertiliTech A/S, Aarhus N (DK)

(72) Inventors: Anton Paarup Kylling, Hinnerup (DK); Jorgen Berntsen, Viborg (DK); Niels Ramsing, Risskov (DK); Soren Porsgaard, Aarhus N (DK); Tine Qvistgaard Kajhoj, Hovedgård (DK); Reidun Berghold Kuhlmann, Knebel (DK)

(73) Assignee: UNISENSE FERTILITECH A/S, Aarhus N (DK)

( * ) Notice: Subject to any disclaimer, the term of this patent is extended or adjusted under 35 U.S.C. 154(b) by 0 days.

(21) Appl. No.: 15/125,140

(22) PCT Filed: Feb. 12, 2015

(86) PCT No.: PCT/EP2015/052991
§ 371 (c)(1),
(2) Date: Sep. 9, 2016

(87) PCT Pub. No.: WO2015/135718
PCT Pub. Date: Sep. 17, 2015

(65) Prior Publication Data
US 2016/0379364 A1   Dec. 29, 2016

(30) Foreign Application Priority Data

Mar. 14, 2014 (GB) .................................. 1404554.6

(51) Int. Cl.
*G06K 9/00* (2006.01)
*G06T 7/00* (2017.01)
(Continued)

(52) U.S. Cl.
CPC ........... *G06T 7/0016* (2013.01); *C12M 21/06* (2013.01); *C12M 41/46* (2013.01); *G06F 3/00* (2013.01);
(Continued)

(58) Field of Classification Search
None
See application file for complete search history.

(56) References Cited

U.S. PATENT DOCUMENTS 8,515,143 B2 * 8/2013 Oonishi ............. G06K 9/00147
382/128
2008/0247628 A1 * 10/2008 Ramsing ............ G06K 9/00127
382/133
(Continued)

FOREIGN PATENT DOCUMENTS

CN    102576027    11/2012
WO    2007/042044    4/2007
(Continued)

OTHER PUBLICATIONS

International Search Report dated Apr. 17, 2015, issued in International Application No. PCT/EP2015/052991.
(Continued)

*Primary Examiner* — Nancy Bitar
(74) *Attorney, Agent, or Firm* — Steptoe & Johnson LLP

(57) ABSTRACT

Apparatus and methods for helping a user establish values (e.g. timings) for a plurality of parameters of interest (e.g. cell divisions) relating to the development of an embryo from a series of images of the embryo are described. For each parameter of interest an image is selected for display to a user seeking to establish a value for the parameter of interest. For example, the selected image may be an image predicted to be an image reflecting the value for the parameter of interest. For example, the selected image may be
(Continued)

based on a calculated timing for a particular developmental event. The timing may be calculated from a numerical analysis of the images or maybe predetermined. If the user is unable to determine a value for the parameter of interest from the selected image, the user may scroll through neighboring images until the user can determine a value for the parameter of interest. A value for the proud of interest may then be established in response to user input, for example a user providing an indication that a timing associated with a currently displayed image from the series of images should be taken to be the value of the parameter of interest. The different parameters of interest may be established in an iterative manner in which an initial image for display to a user is selected for each parameter of interest based on the parameter of interest.

24 Claims, 11 Drawing Sheets

(51) Int. Cl.
| | | |
|---|---|---|
| C12M 3/00 | (2006.01) | |
| C12M 1/34 | (2006.01) | |
| G06F 3/00 | (2006.01) | |
| G06K 9/46 | (2006.01) | |
| G06K 9/62 | (2006.01) | |
| G06K 9/66 | (2006.01) | |
| G06T 11/60 | (2006.01) | |
| G06T 7/246 | (2017.01) | |

(52) U.S. Cl.
CPC ......... *G06K 9/4671* (2013.01); *G06K 9/6215* (2013.01); *G06K 9/66* (2013.01); *G06T 7/246* (2017.01); *G06T 11/60* (2013.01); *G06T 2207/10016* (2013.01); *G06T 2207/30044* (2013.01)

(56) References Cited

U.S. PATENT DOCUMENTS

| | | | |
|---|---|---|---|
| 2010/0195877 A1 | 8/2010 | Oonishi et al. | |
| 2013/0260360 A1* | 10/2013 | Baurmann | G06F 3/14 434/365 |
| 2015/0169842 A1* | 6/2015 | Porsgaard | C12M 21/06 702/19 |
| 2015/0346187 A1* | 12/2015 | Loewke | G01N 33/4833 600/34 |

FOREIGN PATENT DOCUMENTS

| | | |
|---|---|---|
| WO | 2008/154317 | 12/2008 |
| WO | 2011025736 | 3/2011 |
| WO | 2012/047678 | 4/2012 |
| WO | 2014/001312 | 1/2014 |

OTHER PUBLICATIONS

UK Combined Search and Examination Report dated Dec. 24, 2014, issued in GB Application No. 1404554.6.
Office Action from CN 20150014122.9 dated Nov. 21, 2018 (with English Translation).

* cited by examiner

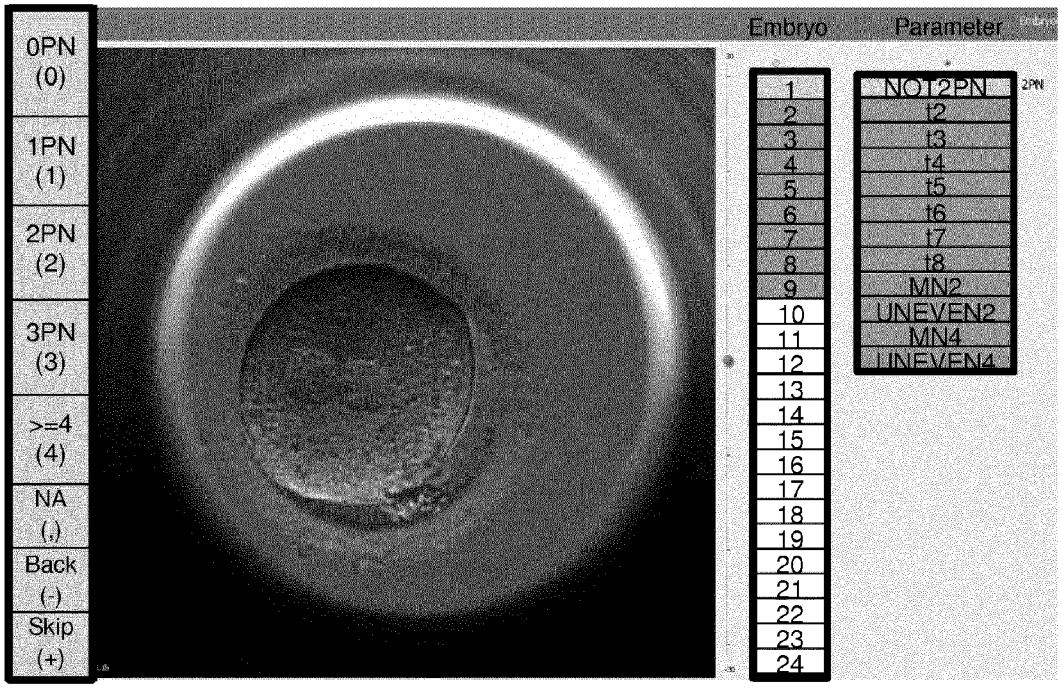
Fig. 5 (NOT2PN assessment)
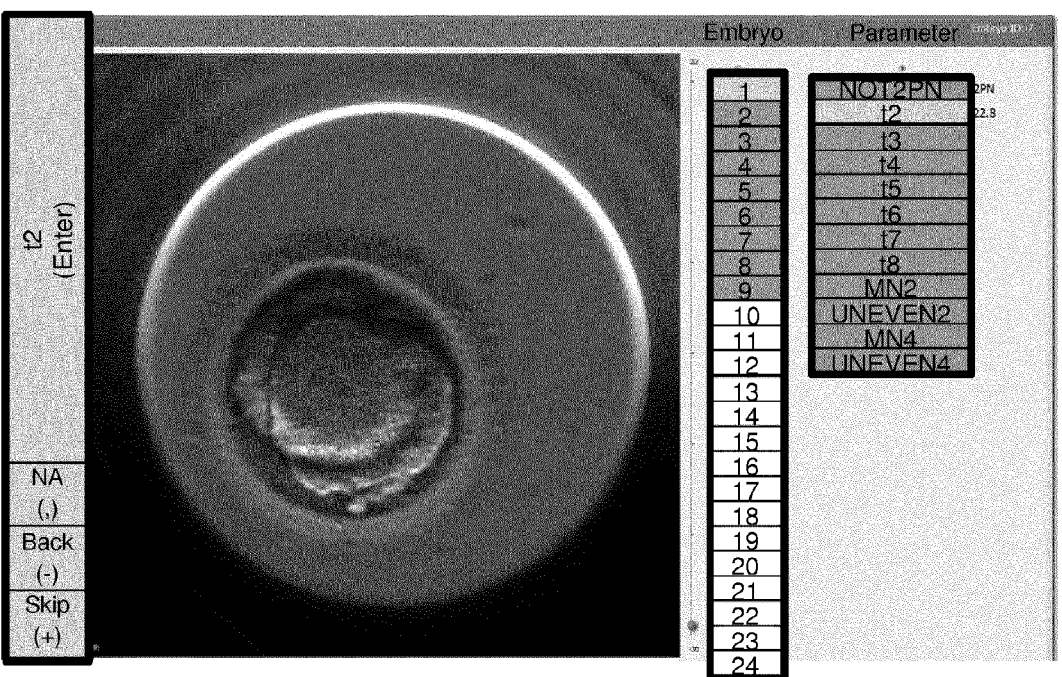
Fig. 6 (t2 annotation)

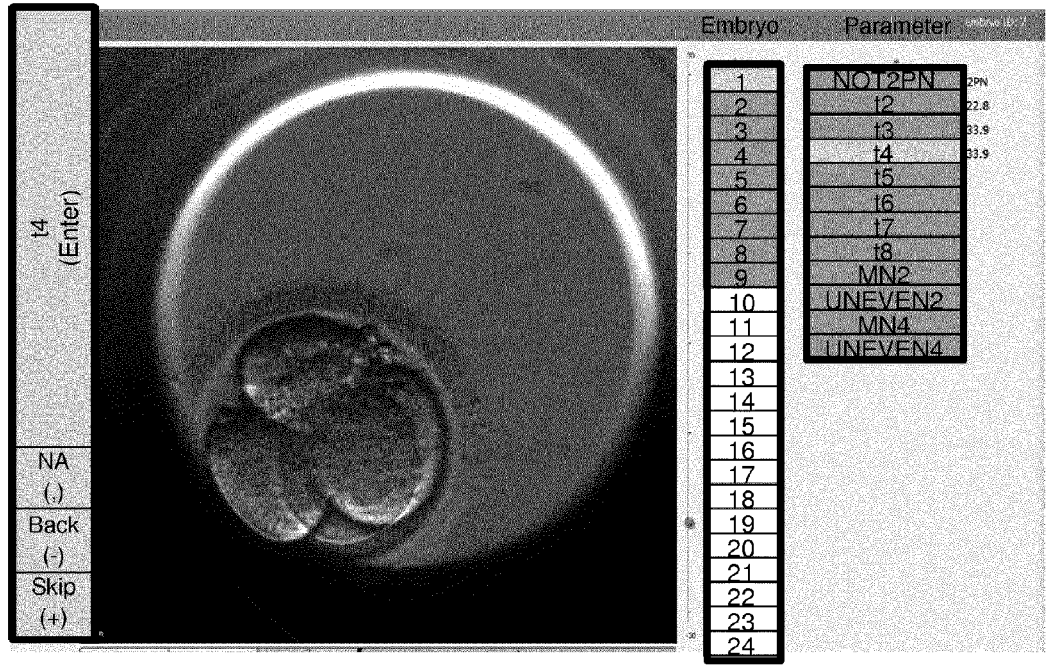
Fig. 7 (t3 & t4 annotation)
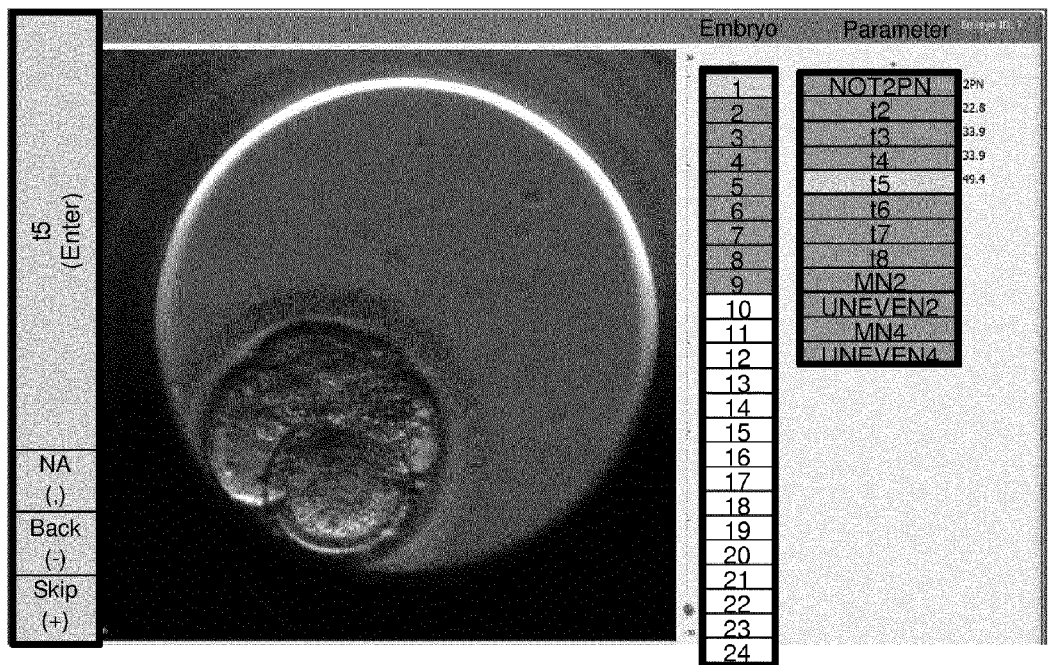
Fig. 8 (t5 annotation)

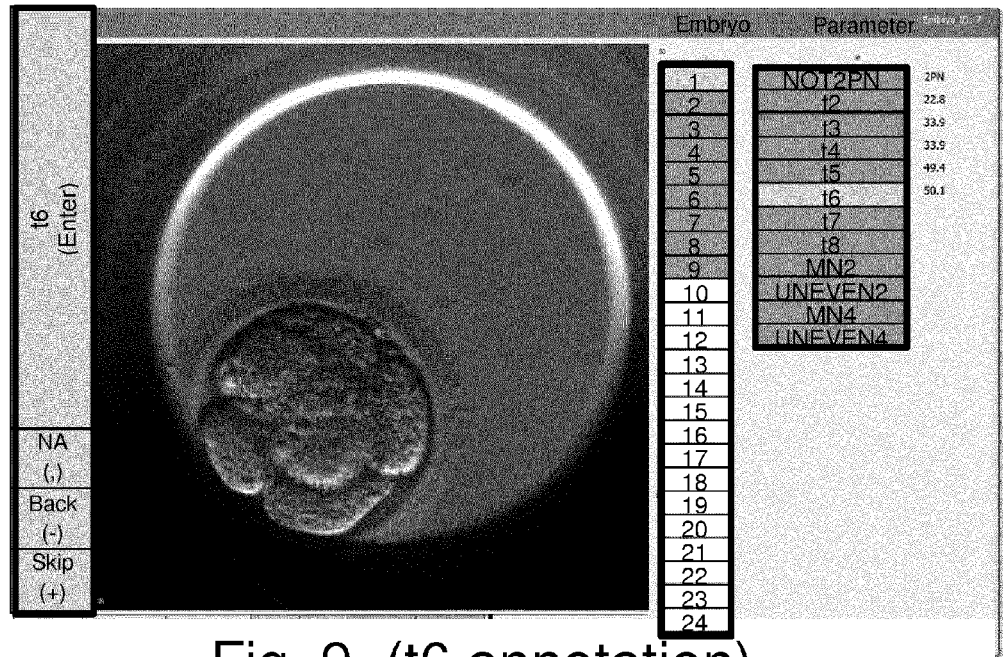
Fig. 9 (t6 annotation)
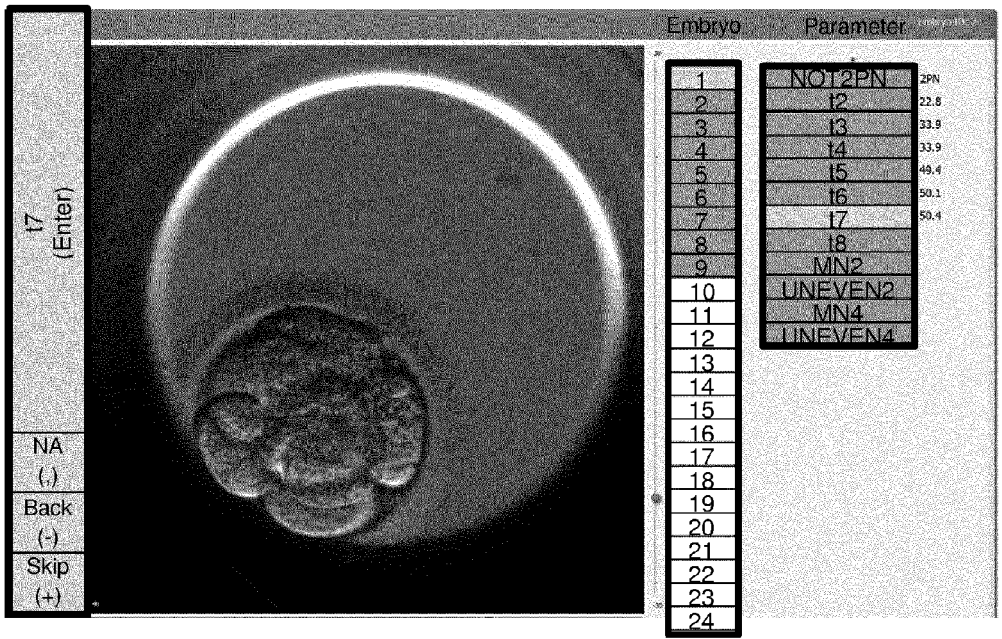
Fig. 10 (t7 annotation)

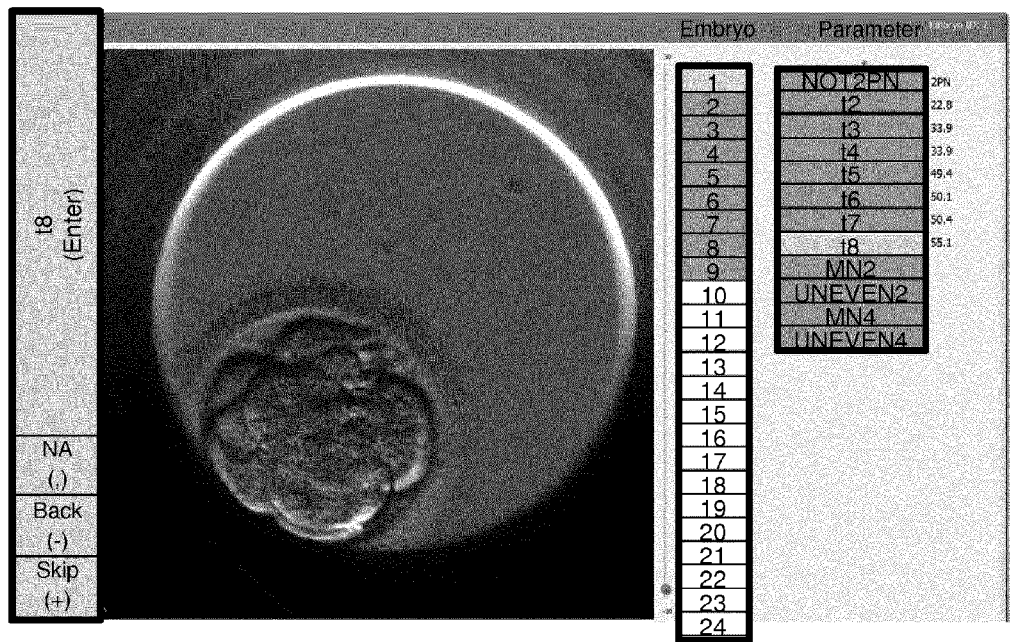
Fig. 11 (t8 annotation)
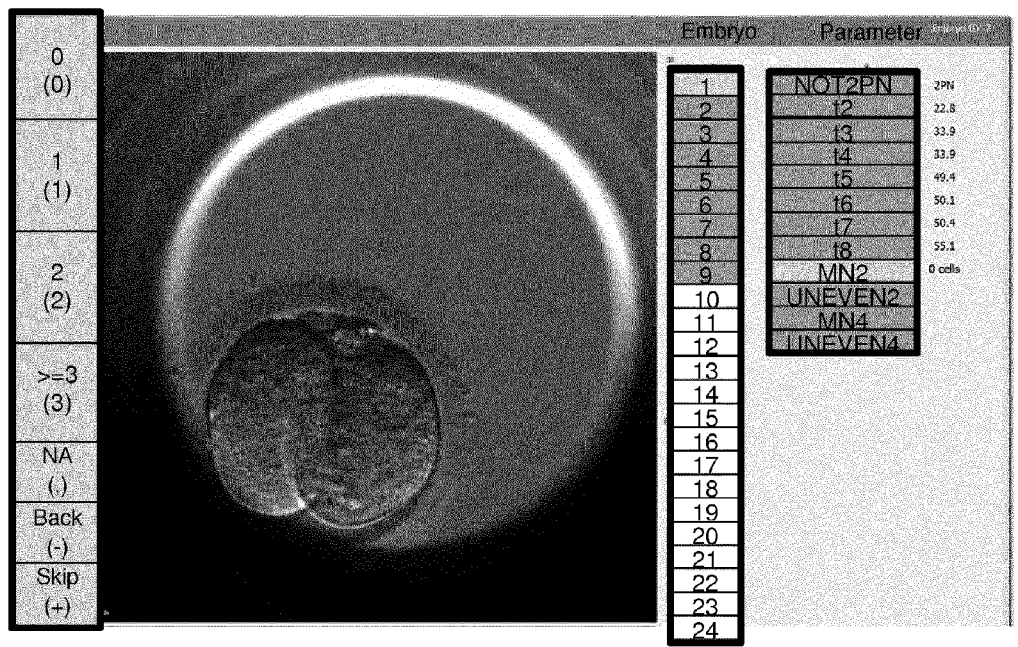
Fig. 12 (MN2 assessment)

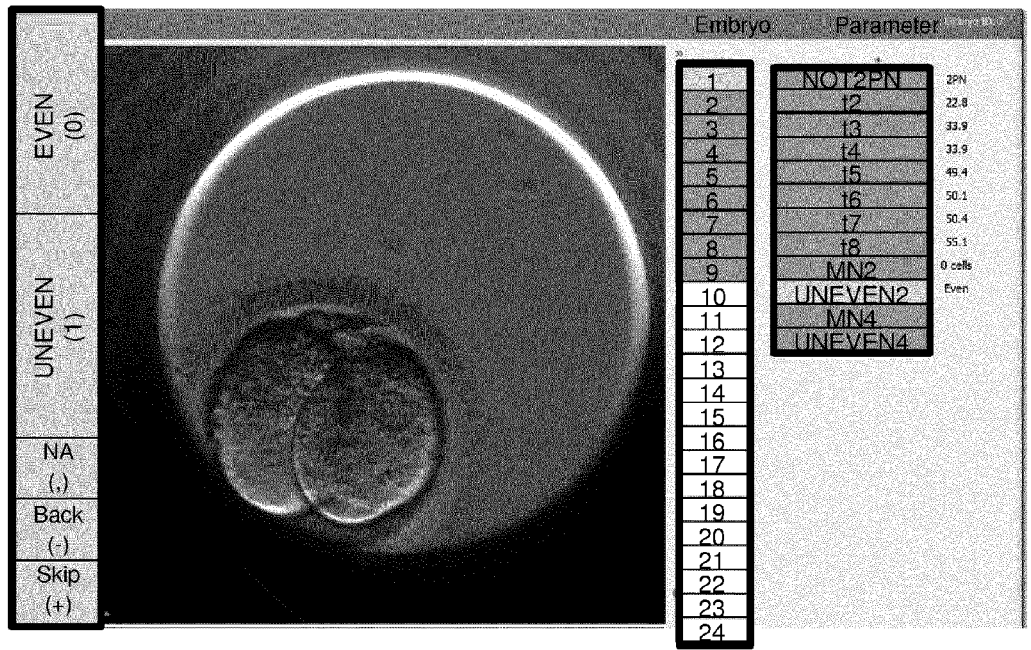
Fig. 13 (2 cell evenness assessment)
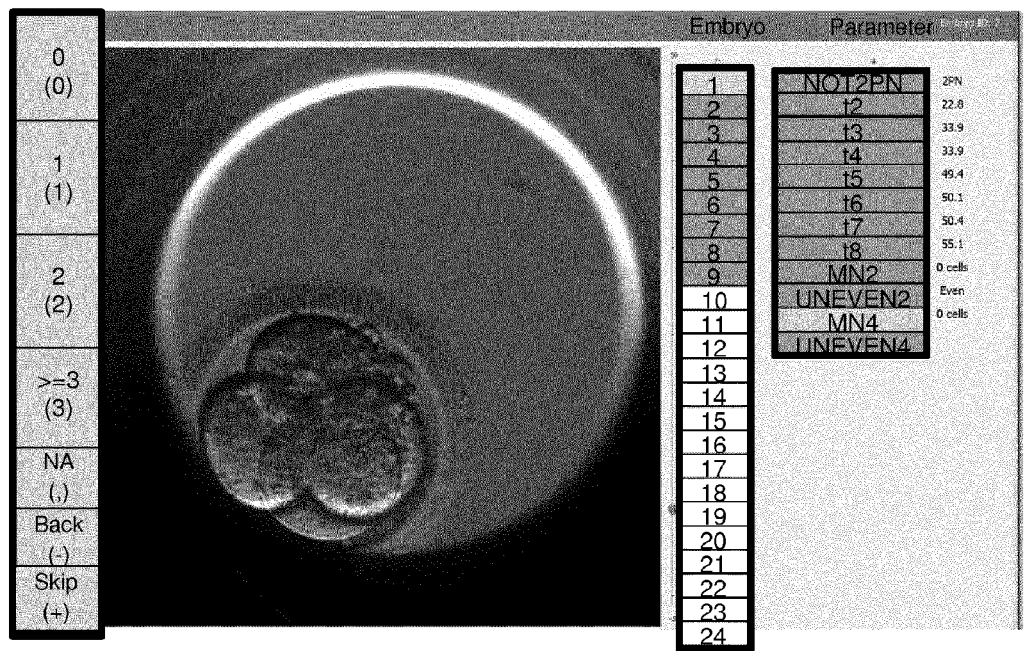
Fig. 14 (MN4 assessment)

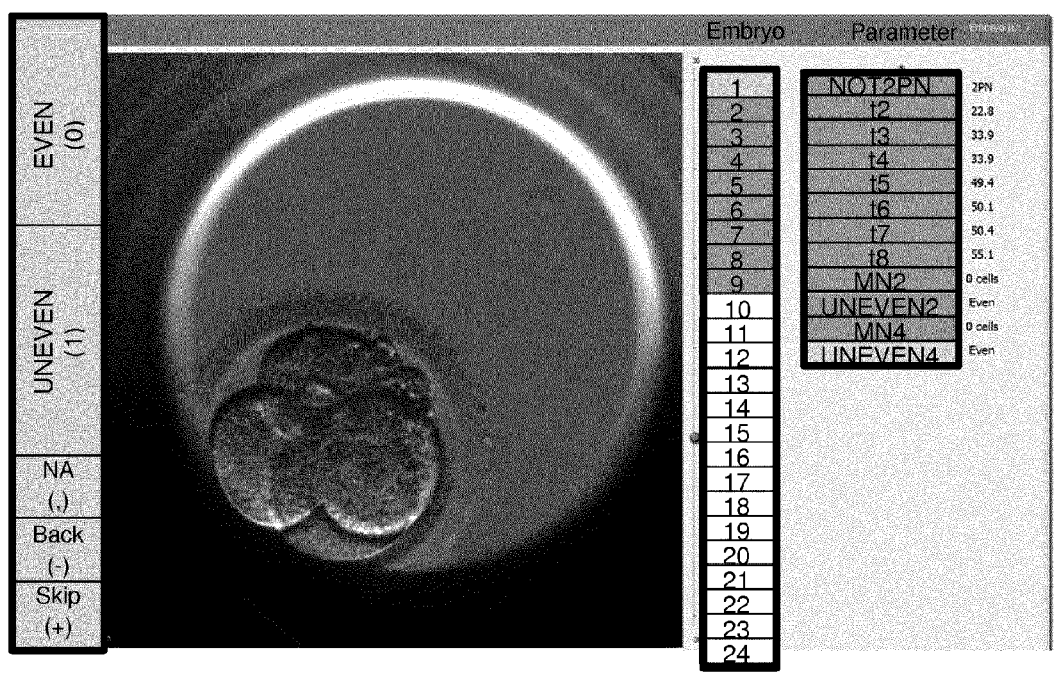
Fig. 15 (4 cell evenness assessment)

| Well | Dec. | Current Score | NOTZPN | C2 | C3 | M | C5 | M6 | C7 | C8 | MM2 | UNEVEN2 | MM4 | UNEVEN4 |
|---|---|---|---|---|---|---|---|---|---|---|---|---|---|---|
| 1 | | NA | 2PN | 27.8 | 30.2 | 39.2 | 51.1 | 57.7 | 62.4 | 62.7 | 0 cells | Uneven | 0 cells | Even |
| 2 | | NA | 2PN | 22.1 | 32.2 | 37.2 | 43.5 | 44.5 | 66.7 | 67.4 | 1 cell | Uneven | 0 cells | Uneven |
| 3 | | NA | | | | | | | | | | | | |
| 4 | | NA | 2PN | 22.8 | 36.9 | 37.5 | | | | | 2 cells | Even | | |
| 5 | | NA | | | | | | | | | | | | |
| 6 | | NA | | | | | | | | | | | | |
| 7 | | NA | 2PN | 22.8 | 33.9 | 34.2 | 49.1 | 50.1 | 55.1 | 55.4 | 1 cell | Even | 0 cells | Even |
| 8 | | NA | 2PN | 20.4 | 29.9 | 32.2 | 40.9 | 42.2 | 46.8 | 49.8 | 0 cells | Even | 0 cells | Even |
| 9 | | NA | 2PN | 22.8 | 32.2 | 32.5 | 44.2 | 44.5 | 45.2 | 45.5 | 0 cells | Even | 0 cells | Even |

FIG. 16

METHODS AND APPARATUS FOR ANALYSING EMBRYO DEVELOPMENT

CLAIM OF PRIORITY

This application claims the benefit under 35 USC 371 to International Application No. PCT/EP2015/052991, filed Feb. 12, 2015, which claims priority to GB Patent Application No. 1404554.6, filed Mar. 14, 2014, each of which is incorporated by reference in its entirety.

BACKGROUND OF THE INVENTION

The present invention relates to methods and apparatus for analysing embryo development. In particular, some embodiments relate to methods and apparatus for establishing values for a plurality of parameters (variables/indicators) relating to the development of an embryo, for example, timings for certain cell division events.

Infertility affects more than 80 million people worldwide. It is estimated that 10% of all couples experience primary or secondary infertility. In vitro fertilization (IVF) is an elective medical treatment that may provide a couple who has been otherwise unable to conceive a chance to establish a pregnancy. It is a process in which eggs (oocytes) are taken from a woman's ovaries and then fertilized with sperm in the laboratory. The embryos created in this process are then placed into the uterus for potential implantation. In between fertilization (insemination) and transfer the embryos are typically stored in an incubation chamber of an incubator for 2-6 days during which time they may be regularly monitored, for example through imaging, to assess their development. Conditions within the incubator, such as temperature and atmospheric composition, are controlled, generally with a view to emulating the conditions in the oviduct and uterus.

In a typical IVF cycle a number of eggs from a single patient will be fertilized and the resulting embryos incubated. However, it is usual for not all incubated embryos to be transferred to the patient's uterus. This is to reduce the risk of potentially dangerous multiple births. Embryos will typically be selected for transfer on the basis of an assessment of the development potential of the embryos that have been incubated. Embryos determined to have the greatest potential for developing into a live birth will be preferentially selected over other embryos in their cohort. Accordingly, an important aspect of IVF treatment is assessing development potential of the embryos comprising a cohort, i.e. determining embryo quality where embryo quality is a prediction representing the likelihood of an embryo successfully implanting, developing in the uterus after transfer and leading to the birth of a healthy baby.

A powerful tool for assessing embryo quality that has recently been developed is time-lapse embryo imaging. Time-lapse embryo imaging involves obtaining images of embryos during their development. This can allow the timings of various developmental events, such as cell divisions, to be established. These timings may sometimes be referred to as morphokinetic parameters for the embryo. Studies have shown how the timings and durations of various embryonic development events can be correlated with development potential for an embryo. For example, a relatively early time of division from one cell to two cells has been found to be an indicator of a good quality embryo. Other morphokinetic parameters, for example the degree of synchronicity in the two divisions when dividing from two cells to four cells, are also found to be sensitive to embryo quality. More generally, there has been proposed various approaches for assessing the development potential of an embryo from parameters relating to the embryo's in-vitro development. Consequently it can be important when assessing embryo quality using time-lapse imaging to establish values for various parameters relating to the timings of various embryo development events and/or other characteristics relating to the development of the embryo, for example in terms of cell-uniformity (evenness) at different stages, the appearance of pro-nuclei (PN), and the presence of multinucleation (MN). To establish values for parameters relating to embryo development from a series of time-lapse images a user will typically view the series of time-lapse images as a movie to identify the images (and hence timings) associated with events of interest and to identify images in which other characteristics (such as unevenness, PN appearance, and MN) can be assessed. This process of establishing values for parameters of interest from a time-lapse series of images is sometimes called annotation.

One well-known apparatus for performing time-lapse embryo imaging is the EmbryoScope® device and associated EmbryoViewer® software developed by, and available from, Unisense FertiliTech A/S (Aarhus, Denmark).

Annotation is generally performed by skilled embryologists and can take a relatively long time to perform. This is because in addition to making the relevant clinical assessments for the respective parameters of interest, the user needs to navigate through what can be a relatively long series of images, and furthermore will typically do this for a number of different embryos for each patient.

U.S. Pat. No. 7,672,369 B2 [1] discloses an approach in which parameters of interest may be established automatically by comparing simulated images of cell models to observed data. U.S. Pat. No. 7,963,906 B2 [2] also describes schemes for automated image processing of images. While automated methods avoid the need for manual annotation, the corresponding lack of skilled clinical assessment may give cause for concern.

The process of reliably establishing values for parameters of interest relating to the development of embryos from time-lapse images in accordance with current techniques can therefore be a relatively time intensive process. Accordingly there is a desire for schemes which can help a user establish values for a plurality of parameters of interest relating to the development of an embryo from a series of images, for example by helping a user perform the annotations more quickly.

SUMMARY OF THE INVENTION

According to a first aspect of the invention there is provided a method for helping a user establish values for a plurality of parameters (variables/indicators) of interest relating to the development of an embryo from a series of images of the embryo at different times during its development, the method comprising the following steps: (a) selecting a current parameter of interest from among the plurality of parameters of interest; (b) automatically selecting an image from within the series of images to display to a user for use in establishing a value for the current parameter of interest, wherein the image is selected according to the current parameter of interest; (c) displaying the selected image to the user on a display; (d) changing the image displayed on the display by scrolling through the series of images around the selected image in response to user input; and (e) establishing a value for the current parameter of interest in response to user input.

In accordance with some, but not all, embodiments the method may further comprise (f) selecting another parameter of interest as the current parameter of interest, and repeating steps (b) to (e).

In accordance with some embodiments repeating steps (b) to (e) in step (f) comprises also repeating step (f) until values for all parameters of interest have been established.

In accordance with some embodiments the image is automatically selected in step (b) based on an analysis of the series of images.

In accordance with some embodiments the analysis of the series of images comprises determining an indication of an amount of change between images comprising the series of images.

In accordance with some embodiments the image is automatically selected in step (b) according to a predefined association between the images comprising the series of images and the parameters of interest.

In accordance with some embodiments the predefined association is based on comparing predefined timings associated with the respective parameters of interest with timings associated with the respective images.

In accordance with some embodiments the method further comprises helping a user establish values for a plurality of parameters of interest relating to the development of a further embryo from a series of images of the further embryo by (h) selecting a current parameter of interest from among the plurality of parameters of interest for the further embryo; (i) automatically selecting an image from within the series of images of the further embryo to display to a user for use in establishing a value for the current parameter of interest, wherein the image is selected according to the current parameter of interest; (j) displaying the selected image to the user on a display; (k) changing the image displayed on the display to another image from the series of images in response to user input received through the one or more user input devices; (l) establishing a value for the current parameter of interest for the further embryo in response to user input; and (m) selecting another parameter of interest as the current parameter of interest, and repeating steps (i) to (m).

In accordance with some embodiments values for the different parameters of interest for the different embryos are established in turn by: establishing different parameters of interest for one of the embryos and then establishing the different parameters of interest for the other of the embryos; or by establishing a parameter of interest for the different embryos and then establishing another parameter of interest the different embryos.

In accordance with some embodiments the parameters of interest comprise times for developmental events for the embryo.

In accordance with some embodiments the image is automatically selected in step (b) based on a predicted timing for a developmental event associated with the current parameter of interest.

In accordance with some embodiments the values for the parameters of interest are user-classifications of embryo characteristics.

In accordance with some embodiments the image is automatically selected in step (b) based on a predicted timing for an image in which the embryo characteristic associated with the current parameter of interest is predicted to be apparent.

In accordance with some embodiments selecting a current parameter of interest in step (a) and/or selecting another parameter of interest in step (f) is based on user input.

In accordance with some embodiments selecting a current parameter of interest in step (a) and/or selecting another parameter of interest in step (f) is performed automatically by selecting parameters of interest in accordance with a predefined sequence.

In accordance with some embodiments step (f) is automatically performed in response to the user input of step (e).

In accordance with some embodiments a value for the current parameter of interest is determined according to a timing associated with an image from the series of images which is displayed on the display when the user input is received in step (e).

In accordance with some embodiments the method further comprises displaying a representation of the values for the plurality of parameters of interest that have been established.

In accordance with some embodiments the representation of the values for the plurality of parameters of interest that have been established is comprises a tabular representation or a graphical representation of the values for the plurality of parameters of interest that have been established.

In accordance with some embodiments the method further comprises displaying a representation of predicted values for at least some of the plurality of parameters of interest that have not been established.

In accordance with some embodiments the method further comprises the values for the plurality of parameters of interest that have been established and the predicted values for the plurality of parameters of interest that have not been established are represented differently.

In accordance with some embodiments the method further comprises determining a development potential for the embryo from one or more of the values established for the plurality of parameters of interest.

According to a second aspect of the invention there is provided a non-transitory computer program product bearing machine readable instructions for carrying out the method of the first aspect of the invention.

According to a third aspect of the invention there is provided an apparatus loaded with and operable to execute machine readable instructions for carrying out the method of the first aspect of the invention.

According to a fourth aspect of the invention there is provided an apparatus for helping a user establish values for a plurality of parameters of interest relating to the development of an embryo from a series of images of the embryo at different times during its development, the apparatus comprising a processor element and a user interface element comprising a display and one or more user input devices, and wherein the processor element is configured to cause the apparatus to perform the following steps: (a) select a current parameter of interest from among the plurality of parameters of interest; (b) select an image from within the series of images to display to a user for use in establishing a value for the current parameter of interest, wherein the image is selected automatically according to the current parameter of interest; (c) display the selected image to the user on the display; (d) change the image displayed on the display to another image from the series of images in response to user input received through the one or more user input devices; and (e) establish a value for the current parameter of interest in response to user input received through the one or more user input devices.

In accordance with some, but not all, embodiments the apparatus may further be configured to (f) select another parameter of interest as the current parameter of interest, and repeating steps (b) to (e).

It will be appreciated that features and aspects of the invention described above in relation to the first and other aspects of the invention are equally applicable to, and may be combined with, embodiments of the invention according to other aspects of the invention as appropriate, and not just in the specific combinations described above.

BRIEF DESCRIPTION OF THE DRAWINGS

The invention is now described by way of example only with reference to the following drawings in which:

FIGS. 5 to 15 schematically show a computer display at various stages of a computer-implemented method of establishing values for parameters relating to the development of an embryo in accordance with an embodiment of the invention;

FIG. 16 schematically shows a display of values for parameters relating to the development of one or more embryos in accordance with an embodiment of the invention.

DETAILED DESCRIPTION

Figure 1:
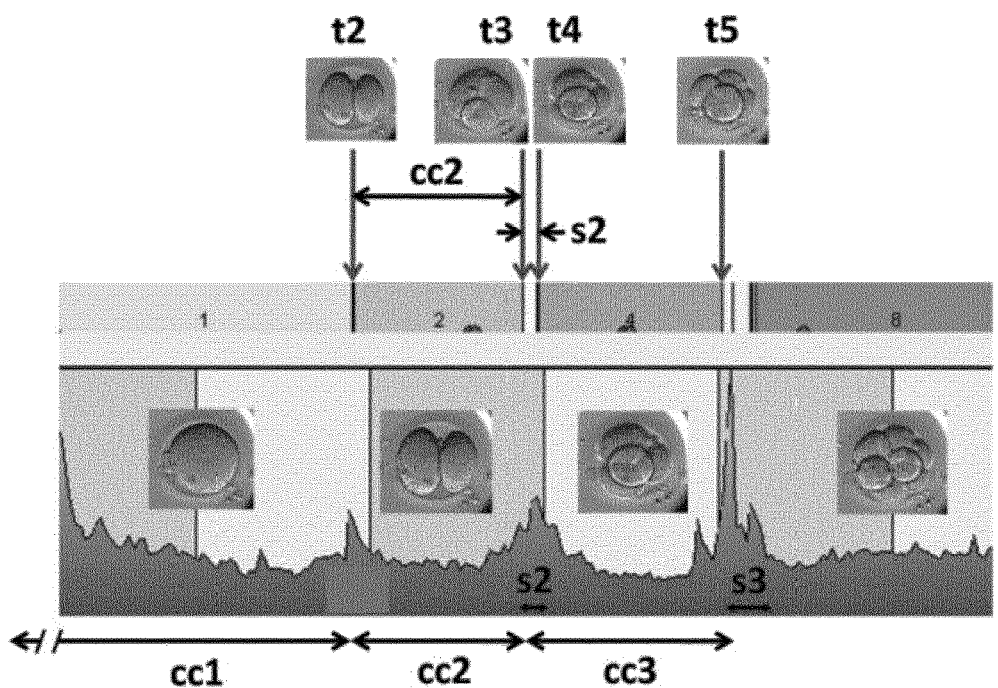
FIG. 1 schematically represents some nomenclature as used herein for an embryo cleavage pattern showing cleavage times (t2 to t5), duration of cell cycles (cc1 to cc3), and synchronies (s2 and s3) in relation to images obtained.

Unless the context demands otherwise, the terms used herein should be interpreted in accordance with their meanings as commonly understood by one of ordinary skill in the art to which this disclosure belongs. Some terms may be used herein in accordance with the following definitions (unless the context demands another meaning).

Cleavage time (cell division time) is defined as the first observed timepoint relative to a defined start point (zero time) when newly formed blastomeres are completely separated by confluent cell membranes, the cleavage time is therefore the time of completion of a blastomere cleavage. In the present context the times are usually expressed as hours post the time of insemination (e.g. the time of Intra-Cytoplasmic Sperm Injection (ICSI), also called microinjection). However, it could also be post the time of mixing of sperm and oocyte (in traditional IVF) or post the time where the successful fusion of gametes to form a new organism (the zygote) is observed for the first time, i.e. exclusion of the second polar body. Similarly, it could be post the time for pronuclear appearance or fading/disappearance or other significant developmental parameter. Cleavage times may thus be defined as follows:

t2: Time of cleavage to 2 blastomere embryo
t3: Time of cleavage to 3 blastomere embryo
t4: Time of cleavage to 4 blastomere embryo
t5: Time of cleavage to 5 blastomere embryo
t6: Time of cleavage to 6 blastomere embryo
t7: Time of cleavage to 7 blastomere embryo
t8: Time of cleavage to 8 blastomere embryo
tn: Time of cleavage to n blastomere embryo The first cell cycle duration cc1 is the period between fertilization and the cleavage time t2 that provides the first pair of daughter cells (i.e. the first second-generation cells). The second cell cycle duration cc2 is the period between the cleavage time t2 that provides the first pair of daughter cells and the cleavage time t3 that provides the first pair of granddaughter cells (i.e. the first third-generation cells). The third cell cycle duration cc3 is the period between the cleavage time t3 that provides the first pair of granddaughter cells and the cleavage time t5 that provides the first pair of great-granddaughter cells (i.e. the first fourth-generation cells). The fourth cell cycle duration cc4 is the period between the cleavage time t5 that provides the first pair of great-granddaughter cells and the cleavage time t9 that provides the first pair of great-great-granddaughter cells (i.e. the first fifth-generation cells).

These cell cycle durations are thus based on the fastest of the blastomeres to divide for each new generation. However, there are additional cell cycle durations associated with division of slower blastomeres.

For example, in addition to cell cycle duration cc2 there is a cell cycle duration cc2b corresponding to the period between the cleavage time t2 that provides the first pair of daughter cells and the cleavage time t4 that provides the second pair of granddaughter cells. In this regard cell cycle duration cc2 may also be referred to as cell cycle duration cc2a for simplicity in terminology.

Furthermore, in addition to cell cycle duration cc3 there is a cell cycle duration cc3b corresponding to the period between the cleavage time t3 that provides the first pair of granddaughter cells and the cleavage time t6 that provides the second pair of great-granddaughter cells. There is also a cell cycle duration cc3c corresponding to the period between the cleavage time t4 that provides the second pair of granddaughter cells and the cleavage time t7 that provides the third pair of great-granddaughter cells. There is also a cell cycle duration cc3d corresponding to the period between the cleavage time t4 that provides the second pair of granddaughter cells and the cleavage time t8 that provides the fourth pair of great-granddaughter cells. In this regard cell cycle duration cc3 may also be referred to as cell cycle duration cc3a for consistency in terminology.

Thus, duration of cell cycles is defined as follows:
cc1=t2: First cell cycle.
cc2 (also referred to cc2a)=t3−t2: Second cell cycle, duration of period as 2 blastomere embryo.
cc2b=t4−t2: Second cell cycle for both blastomeres, duration of period as 2 and 3 blastomere embryo.
cc3 (also referred to cc3a)=t5−t3: Third cell cycle, duration of period as 3 and 4 blastomere embryo.
cc2_3=t5−t2: Second and third cell cycle, duration of period as 2, 3 and 4 blastomere embryo (i.e. cc2+cc3).
cc4=t9−t5: Fourth cell cycle, duration of period as 5, 6, 7 and 8 blastomere embryo.

Synchronicities are defined as follows:
s2=t4−t3: Synchrony in division from 2 blastomere embryo to 4 blastomere embryo.
s3=t8−t5: Synchrony in division from 4 blastomere embryo to 8 blastomere embryo.

s3a=t6−t5; s3b=t7−t6; s3c=t8−t7: Duration of the individual cell divisions involved in the development from 4 blastomere embryo to 8 blastomere embryo.

cc3b, cc3c, cc3d=t6−t3; t7−t4; and t8−t4 respectively: Third cell cycle for slower blastomeres, duration of period as a 3, 4, and 5 blastomere embryo; as a 4, 5 and 6 blastomere embryo, and as a 4, 5, 6 and 7 blastomere embryo respectively.

Figure 2:
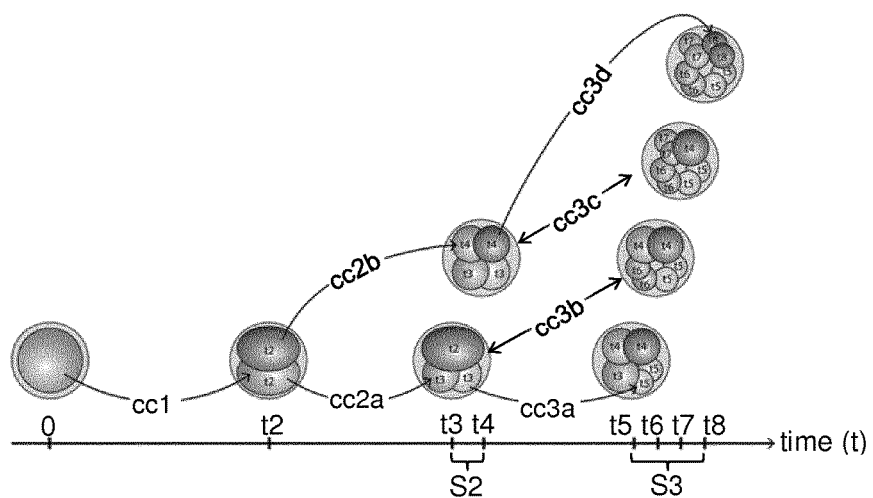
FIG. 2 schematically represents an embryo at different embryo developmental events from initial insemination (at time t=0) and at cleavage times t2-t8 with some associated aspects of timing terminology as used herein.

FIGS. 1 and 2 schematically represent some aspects of the terminology used herein regarding the timings and durations of some embryo developmental events such as discussed above. FIG. 1 shows a number of images of an embryo at various stages of development and indicates various timings associated with various developmental events, such as t2, t3, t4, t5, cc1, cc2 (which may also be referred to herein as cc2a), cc3 (which may also be referred to herein as cc3a), s2 and s3. FIG. 2 schematically represents from left to right the development of the embryo through the one, two, three, four, five, six, seven and eight blastomere stages. The times t2 to t8 at which the respective cell division stage are complete is schematically marked along the bottom axis. FIG. 2 also schematically indicates the cell cycle durations cc1, cc2a, cc2b, cc3a, cc3b, cc3c and cc3d and synchronicities S2 and S3.

Cleavage period is defined as the period of time from the first observation of indentations in the cell membrane (indicating onset of cytoplasmic cleavage) to when the cytoplasmic cell cleavage is complete so that the blastomeres are completely separated by confluent cell membranes. Also termed as duration of cytokinesis.

Fertilization and cleavage may in some respects be considered to be the primary morphological events of an embryo, at least until the 8 blastomere stage or until the start of compaction. Cleavage time, cell cycle, synchrony of division and cleavage period are examples of morphological embryo parameters that can be defined from these primary morphological events and each of these morphological embryo parameters may be defined as the duration of a time period between two morphological events, e.g. measured in hours.

As already mentioned, it is known to establish a measure of a development potential for an embryo from various parameters associated with its development, such as parameters corresponding to (or based on) the timings discussed above, and in order to do this, values for the relevant parameters of interest may be determined from time-lapse images of the embryo as it develops through the relevant stages. In some approaches for determining a development potential for an embryo other developmental characteristics may be of interest. For example, an assessment of the quality of an embryo may take account of values established for the following characteristics:

NOT2PN: Indication of whether or not two pro-nuclei are properly identified for the embryo. This characteristic may be determined visually from an image of the embryo at the appropriate developmental stage and may take values corresponding to "0", "1", "2", "3", or "4 or more" according to the number of pro-nuclei identified for the embryo (a value of "2" is normal).

MN2: Indication of (any) multi-nucleation observed at the two blastomere (cell) stage. This characteristic may be determined visually from an image of the embryo at the appropriate developmental stage and may take values corresponding to "0", "1" or "2" corresponding to the number of cells determined to show multi-nucleation at the two blastomere stage.

MN4: Indication of (any) multi-nucleation observed at the four blastomere stage. This characteristic may be determined visually from an image of the embryo at the appropriate developmental stage and may take values corresponding to "0", "1", "2", "3" or "4" corresponding to the number of cells identified as showing multi-nucleation at the four blastomere stage.

UNEVEN2: Indication of (un)evenness of the blastomeres at the two blastomere stage. This characteristic may be determined visually from an image of the embryo at the appropriate developmental stage and may take values corresponding to "Even" (blastomeres in the two blastomere embryo are classified as being even) or "Uneven" (blastomeres in the two blastomere embryo are classified as being uneven).

UNEVEN4: Indication of (un)evenness of the blastomeres at the four blastomere stage. This characteristic may be determined visually from an image of the embryo at the appropriate developmental stage and may take values corresponding to "Even" (blastomeres in the four blastomere embryo are classified as being even) or "Uneven" (blastomeres in the four blastomere embryo are classified as being uneven).

It will be appreciated the establishment of values for some of these parameters can include an element of subjectivity, for example in respect of whether cells comprising an embryo are even or are not even. It will also be appreciated the terminology adopted for the specific values (e.g. "even", "uneven") is not significant, and the values could equally be characterised in other ways, e.g. as "true" or "false" of by numerical values associated with the different potential states, e.g. "0" for even, "1" for uneven).

Embryo quality is a measure of the ability of an embryo to successfully implant and develop in the uterus after transfer. Embryos of high quality have a higher probability of successfully implanting and developing in the uterus to a healthy baby after transfer than low quality embryos. However, even a high quality embryo is not a guarantee for implantation as the actual transfer and the woman's receptivity influences the final result.

Viability and quality may be used interchangeably. Embryo quality (or viability) measurement is a parameter intended to reflect the quality (or viability) of an embryo such that embryos with certain values of the quality parameter (e.g. high or low values depending on how the parameter is defined) have a high probability of being of high quality (or viability), and low probability of being low quality (or viability). Whereas embryos with certain other values for the quality (or viability) parameter have a low probability of having a high quality (or viability) and a high probability of being low quality (or viability)

The term "developmental potential" may be used to reflect an estimated likelihood of an embryo to develop to blastocyst stage, to implant, to result in pregnancy, and/or to result in a live-born baby. In some embodiments the development potential may be a determination of embryo quality. Developmental potential may be equated with embryo quality. An embryo having a positive developmental potential (i.e. a good (high) embryo quality) is one that is more likely develop to blastocyst stage and/or result in successful implantation and/or develop in the embryo in the uterus after transfer and/or result in pregnancy and/or result in a live-born baby as compared to an embryo having a negative developmental potential (or poor (low) embryo quality).

Thus embryos determined to be of good (high) quality are determined to have a higher probability of successfully implanting and/or of developing in the uterus after transfer compared with low quality embryos. However, it will be appreciated a high quality embryo is not a guarantee for implantation as the actual transfer and the woman's receptivity highly influences the final result.

In some cases the term "embryo" may be used to describe a fertilized oocyte after implantation in the uterus until 8 weeks after fertilization, at which stage it become a fetus. According to this definition the fertilized oocyte is often called a pre-embryo or zygote until implantation occurs. However, the term "embryo" as used herein will have a broader definition, which includes the pre-embryo phase. The term "embryo" as used herein encompasses all developmental stages from the fertilization of the oocyte through morula, blastocyst stages, hatching and implantation. Accordingly, the term embryo may be herein to denote each of the stages fertilized oocyte, zygote, 2-cell, 4-cell, 8-cell, 16-cell, compaction, morula, blastocyst, expanded blastocyst and hatched blastocyst, as well as all stages in between (e.g. 3-cell or 5-cell).

An embryo is approximately spherical and is composed of one or more cells (blastomeres) surrounded by a gelatine-like shell, the acellular matrix known as the zona pellucida. The zona pellucida performs a variety of functions until the embryo hatches, and is a good landmark for embryo evaluation. The zona pellucida is spherical and translucent, and should be clearly distinguishable from cellular debris.

An embryo is formed when an oocyte is fertilized by fusion or injection of a sperm cell (spermatozoa). The term embryo is traditionally used also after hatching (i.e. rupture of zona pellucida) and the ensuing implantation. For humans the fertilized oocyte is traditionally called a zygote or an embryo for the first 8 weeks. After that (i.e. after eight weeks and when all major organs have been formed) it is called a fetus. However the distinction between zygote, embryo and fetus is not generally well defined. The terms embryo and zygote may be used herein interchangeably.

An embryo that is analysed in accordance with embodiments of the invention such as described herein may be previously frozen, e.g. embryos cryopreserved immediately after fertilization (e.g. at the 1-cell stage) and then thawed. Alternatively, they may be freshly prepared, e.g. embryos that are freshly prepared from oocytes by IVF or ICSI techniques for example. It will be appreciated that in so far as an embryo's development has been halted by freezing, the timings of developmental events after fertilization may be defined by ignoring the time between freezing and thawing. Alternatively, a starting time may be defined as one of the first developmental events, such as exclusion of second polarbody or appearance/disappearance of pronuclei, post thawing.

Fertilization may be considered to be the time point where the sperm cell is recognized and accepted by the oocyte. The sperm cell triggers egg activation after the meiotic cycle of the oocyte has been suspended in metaphase of the second meiotic division. This results in the production and extrusion of the second polar body. Some hours after fusion of sperm and ovum, DNA synthesis begins. Male and female pronuclei (PN) appear. The PN move to the center of the egg and the membranes breakdown and the PN disappear (fade). This combination of the two genomes is called syngamy. Hereafter, the cell divisions begin.

The time when the pronuclei disappear may be referred to as t2PN. The terms "fade(d)" and "disappear(ed)" in relation to the pro-nuclei (PN) may be used herein interchangeably.

During embryonic development, blastomere numbers increase geometrically (1-2-4-8-16- etc.). Synchronous cell cleavage is generally maintained to the 8-cell stage or later, until compaction in human embryos. After that, cell cleavage becomes asynchronous and finally individual cells possess their own cell cycle. Human embryos produced during infertility treatment can be transferred to the recipient before 8-blastomere stage. In some cases human embryos are also cultivated to the blastocyst stage before transfer. This is preferably done when many good quality embryos are available or prolonged incubation is necessary to await the result of a pre-implantation genetic diagnosis (PGD). However, there is a tendency towards prolonged incubation as incubation technology improves.

Some example implementations of embodiments of the invention may be used to establish blastocyst related parameters.

A blastocyst quality criterion/measure is an example of an embryo quality criterion/measure. The blastocyst quality criteria may, for example, relate to the development of the embryo from compaction, i.e. initial compaction, to the hatched blastocyst. Compaction is a process wherein an intensification of the contacts between the blastomeres with tight junction and desmosomes result in reduction of the intercellular space and a blurring of the cell contours. Before compaction the blastomeres of the embryo can be followed individually and before compaction the embryo development follows a route of distinct and mostly synchronous cell divisions that can be observed by the naked eye and readily annotated. After compaction the embryo development is characterized by a more or less continuous development from morula to blastocyst, where individual blastomeres become difficult to track, but a number of stages may nonetheless be characterised by establishing values for parameters associated with these stages by visual inspection of images obtained for the relevant development stages.

Start of compaction (SC) describes the first time a compaction between two or more blastomeres is observed. Thus, SC marks the initiation of the compaction process.

Morula (M) is associated with the first time where no plasma-membranes between blastomeres are visible. When the compaction process is complete no plasma-membranes between any of the blastomeres forming the compaction are visible and the embryo can be defined as a morula. Most often Morula is seen after the third synchrony period S3 (i.e. after t8) close to, or right in the beginning, of the fourth synchrony period S4 (i.e. at t9), but may be earlier. Rarely do embryos cleave to 16 cells or more before compaction is initiated in human embryos.

Initial differentiation of trophectoderm (IDT) is defined as the first time where distinct trophectoderm cells are recognized. Start of blastulation (SB) is defined as the first time a fluid-filled cavity, the blastocoel, can be observed. It is also referred to as "Onset of cavitation". It describes the initiation of the transition period between the morula stage and the blastocyst stage of the embryo. Embryos often remain in this transition stage for a period of time before entering the actual blastocyst stage. The onset of cavitation usually appears immediately after differentiation of the trophectoderm cells. The outer layer of the morula with contact to the outside environment begins to actively pump salt and water into the intercellular space, as a result of which a cavity (the blastocoel) begins to form.

Blastocyst (B) may be defined as where there is a clear distinction between trophectoderm and inner cell mass cells.

Initial differentiation of inner cell mass (IDICM) defined as the first time the inner cell mass can be recognized. IDICM describes the initiation of inner cell mass development. An eccentrically placed cluster of cell connected of gab junction where the boundaries between the cells seem not well defined.

Onset of expansion of the blastocyst (EB) may be defined as the first time the embryo has filled out the periviteline space and starts moving/expanding Zona Pelucidae. EB may describe the initiation of the embryo's expansion. As the blastocyst expands the zona pellucida becomes visibly thinner.

Hatching blastocyst (HB) may be defined as the first time a trophectoderm cell has escaped/penetrated the zona pellucida or a certain fraction have hatched.

Fully hatched blastocyst (FH) is defined as when hatching is completed with shedding zona pellucida.

Various timings associated with blastocyst development may be defined as follows:

tM=Time from insemination to formation of morula (hours)

tSB=Time from insemination to start of blastulation (hours)

tB=Time from insemination to formation of blastocyst (hours)

tEB=Time from insemination to formation of expanded blastocyst (hours)

tHB=Time from insemination to hatching blastocyst (hours)

Such timings also represent parameters of interest for which values may be established in accordance with some embodiments of the invention as described herein.

Figure 3:
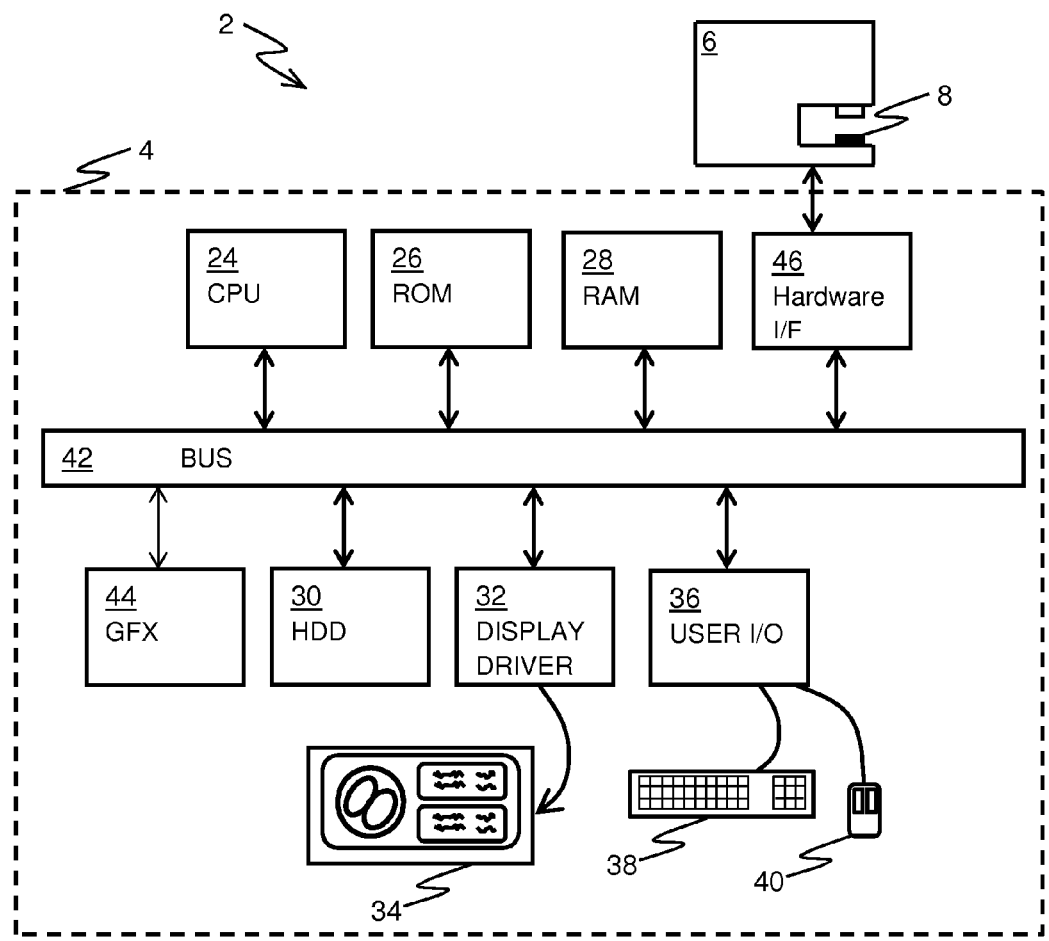
FIG. 3 schematically represents an apparatus for establishing values for parameters relating to the development of one or more embryos in accordance with an embodiment of the invention.

FIG. 3 schematically represents an apparatus 2 for assisting a user establish values for parameters relating to the development of an embryo 8 in accordance with certain embodiments of the invention. The apparatus 2 comprises a general purpose computer 4 coupled to an embryo imaging system 6. The embryo imaging system 6 may be generally conventional and is configured to obtain images of the embryo 8 at various stages of development in accordance with established techniques. It will be appreciated that in general the embryo imaging system 6 will typically be configured to obtain images of a plurality of embryos, rather than just a single embryo, over a monitoring period. For example, a typical study may involve the analysis of a number of embryos, for example 72 embryos. The embryo imaging system may be configured to record images of each embryo (potentially with images being taken in multiple focal planes) one at a time before moving on to image the next embryo. Once all embryos have been imaged, which might, for example, take 5 minutes, the cycle of imaging the individual embryos may be repeated to provide respective images for the respective embryos for the next time point.

The general purpose computer 4 is adapted (programmed) to execute a method for helping a user establish values for a plurality of parameters of interest relating to the development of an embryo from a series of images of the embryo obtained at different times during its development as described further herein.

Thus the computer system 4 is configured to perform processing of embryo image data in accordance with an embodiment of the invention. The computer 4 includes a central processing unit (CPU) 24, a read only memory (ROM) 26, a random access memory (RAM) 28, a hard disk drive 30, a hardware interface 46, a display driver 32 and display screen 34 and a user input/output (IO) circuit 36 with a keyboard 38 and mouse 40. These devices are connected via a common bus 42. The computer 4 also includes a graphics card 44 connected via the common bus 42. The graphics card includes a graphics processing unit (GPU) and random access memory tightly coupled to the GPU (GPU memory). The embryo imaging system 6 is communicatively coupled to the computer 4 via the hardware interface 46 in accordance with conventional technical techniques.

The CPU 24 may execute program instructions stored within the ROM 26, the RAM 28 or the hard disk drive 30 to carry out processing of embryo image data that may be stored within the RAM 28 or the hard disk drive 30. The RAM 28 and hard disk drive 30 are collectively referred to as the system memory. In some implementations, processing in accordance with embodiments of the invention may be based on embryo images obtained by the computer 4 directly from the imaging system 6. In other implementations, processing in accordance with embodiments of the invention may be based on embryo images previously obtained and stored in a memory of the computer 4, e.g. in RAM 28 of HDD 30 (i.e. the embryo imaging system 6 itself is not a required element of embodiments of the invention). Aspects of the computer 4 may largely be conventional except that the CPU is configured to run a program, which may for example be stored in RAM 28, ROM 26 or HDD 30, to perform processing in accordance with certain embodiments of the invention as described herein. Some aspects of the processing, for example image processing, may in some examples be run in the GPU.

The embryo 8 in accordance with certain example implementations is monitored regularly using the embryo imaging system 6 to obtain a series of time-lapse images (typically the embryo imaging system will obtain a series of time-lapse images for a plurality of embryos, for example for up to 6 patients with up to 12 embryos per patient). The embryo is preferably monitored (imaged) at least once per hour, such as at least twice per hour, such as at least three times per hour, such as at least four times per hour, such as at least six times per hour, such as at least 12 times per hour. The monitoring is preferably conducted while the embryo is situated in an incubator used for culturing the embryo. This may be carried out through image acquisition of the embryo in accordance with any established time-lapse methods.

In a general sense, various methods described herein in accordance with certain embodiments of the invention are based on assisting a user annotate events associated with the development of an embryo (i.e. establishing values for parameters of interest relating to an embryo's development, such as timings for particular cell division events and/or classifications of characteristics of the embryo, such as evenness, presence of multi-nucleation).

In common with conventional techniques, a user may establish values for parameters of interest for an embryo from a visual inspection of images comprising a time-lapse series of images for the embryo. The images are displayed on the display screen 34 of the apparatus 2. However, and as discussed further below, in accordance with certain embodiments of the invention, in order to assist a user establish a value for a particular parameter of interest, an image from the series of images is automatically selected as an initial image to display to the user based on the particular parameter of interest. The user may then, if necessary, scroll backwards and/or forwards through the images around the automatically selected image in the timeseries until the user is able to establish a value for the parameter of interest. For example, if a current parameter of interest is t3 (i.e. the user is in the process of establishing a timing associated with the division to three cells), an image from the series of images is automatically selected based on the current parameter of interest being t3. The user may then scroll/step through the images starting from the initial image to identify the time at which the cell divides to three cells. When the user identifies an image which is considered to correspond with t3 (e.g. based on the user's clinical knowledge), user may provide an input to indicate this (e.g. by pressing a button on the keyboard 38 or mouse 40, or other user input device). The actual clinical determination of the value for the relevant parameter may be made in accordance with conventional techniques. However, what is different in accordance with certain embodiments as compared to existing techniques is a manner in which the images comprising the series of images are presented to a user and a manner in which the user indicates a value for a particular parameter. In particular, in accordance with existing techniques, a user would typically play the series of images as a movie (or flick through a stack of images) until a point is reached at which a value for one of the parameters of interest can be established, and the user would then provide input to identify both what the parameter is and its value.

Figure 4:
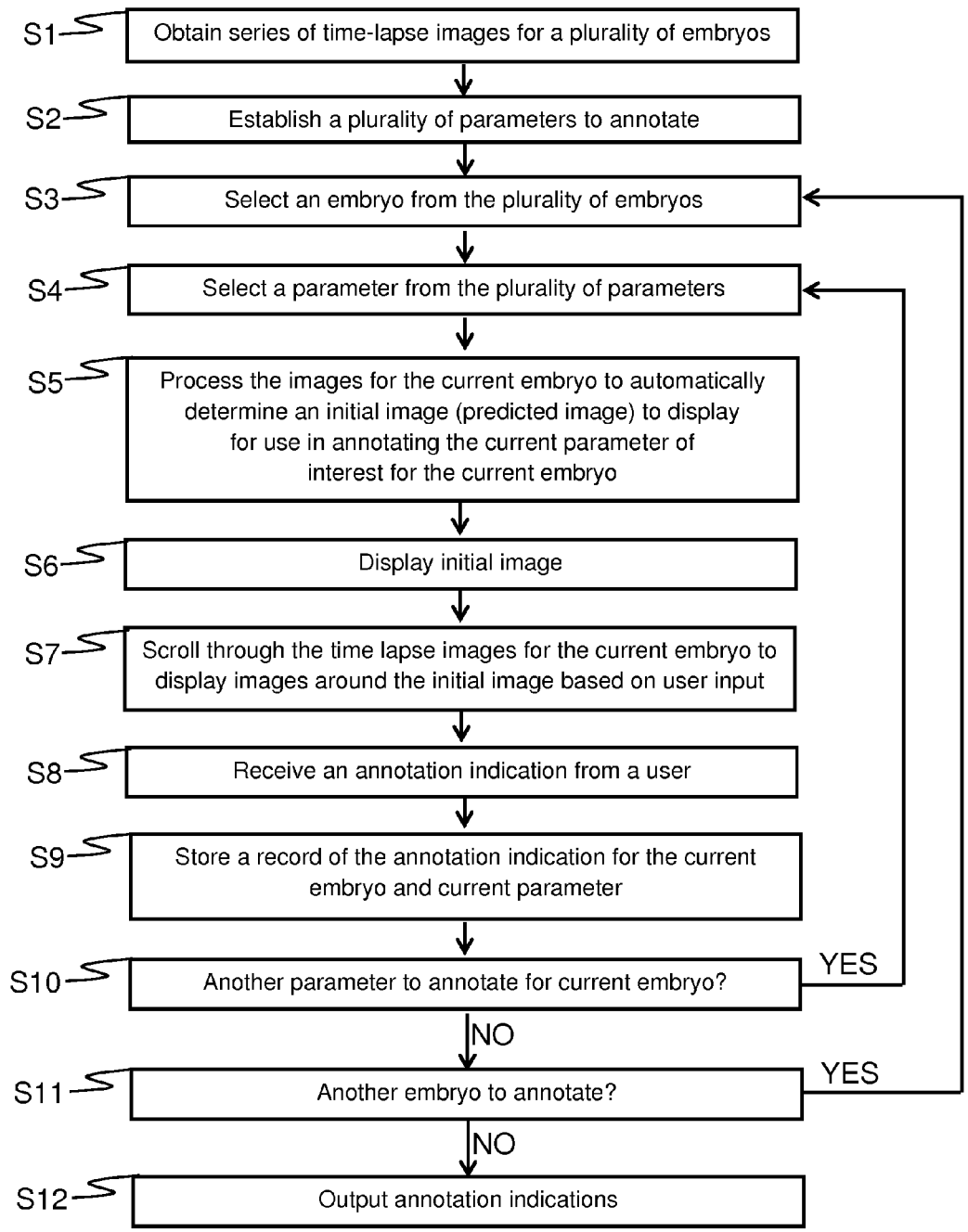
FIG. 4 schematically represents a method for establishing values for parameters relating to the development of one or more embryos in accordance with an embodiment of the invention.

FIG. 4 is a flow diagram which schematically represents methods for establishing values for parameters relating to the development of one or more embryos in accordance with some embodiments of the invention. The method performed in accordance with FIG. 4 is a computer-implement method involving user input and which may be implemented using the computer 4 of FIG. 3 with the CPU 24 implementing the method in accordance with a loaded program. In broad summary, the method involves, for each parameter of interest, selecting an image to be initially presented to a user from a series of images associated with time-lapse monitoring of the developing embryo. The initial image to be presented to the user for a particular parameter of interest is automatically selected (i.e. the selection is made by the computer rather than by the user) depending on the current parameter of interest. The aim is for the initial image to provide the user with a good starting point for establishing a value for the relevant parameter (i.e. the parameter for which the particular initial image has been automatically selected). The user may then, if necessary, change the displayed image from the initial image to another image by providing user input to step forwards and/or backwards through the series of images to allow the user make a clinical judgement for establishing the relevant parameter of interest. Once the user has made the relevant clinical judgement for the current parameter of interest, the user may provide input to indicate a value established for this parameter according to the user's clinical judgement, and this value may be stored. This process may repeat iteratively for each parameter of interest for a given embryo and/or for a given parameter of interest for a plurality of different embryos.

Thus, in step S1 a series of time-lapse images for a plurality of embryos is obtained. In this example it will be assumed the method is being implemented to analyse time-lapse images from 9 embryos from a single patient. Typically step S1 will be performed by loading the respective images from storage, such as HDD 30, for processing in accordance with methods as described here in. The original source of the series of images is not significant. The images may be from an imaging apparatus coupled to the apparatus implementing the method, for example, the imaging apparatus 6 coupled to the computer 4 in the arrangement of FIG. 3. Alternatively, the images may have been previously obtained from an unrelated imaging apparatus and transferred to the HDD 30. The images may generally be conventional.

In step S2 a plurality of parameters of interest which are to be annotated for the current study are established. This will depend on the particular implementation at hand. Different approaches for assessing the development potential for embryos may make use of different morphokinetic parameters. Accordingly, the plurality of parameters established in step S2 will depend on the specific implementation at hand (i.e. based on the parameters desired for whichever approach for assessing the development potential of embryos is to be used). Typically the plurality of parameters of interest will be predefined, for example based on a bespoke configuration for a particular clinic implementing the method according to their preferred techniques for assessing embryo quality, or may be fixed by a supplier of an apparatus/computer program configured to implement the method. In principle, a user could be provided with an opportunity to select the parameters of interest for a particular study. The establishment of the parameters of interest to annotate may also be based on characteristics of the series of images. For example, the computer 4 may be configured to automatically determined parameters of interest for annotation based on a duration of the respective timeseries for the respective embryos. For example, the parameters to annotate for a timeseries spanning five days will generally be different from the parameters to annotate for a timeseries spanning three days (because there will be additional parameters for developmental events occurring on the fourth and fifth days).

For this particular example implementation it is assumed the plurality of parameters of interest to be established (or at least attempted to be established) for the embryos currently under study comprise a plurality of timings and a plurality of morphological characteristics. The timings of interest are assumed to be t2, t3, t4, t5, t6, t7 and t8 (as defined above) and the morphological characteristics of interest are assumed to be NOT2PN, MN2, UNEVEN2, MN4 and UNEVEN4 (again as defined above). Thus in this example there are a total of 12 parameters of interest. However, it will be appreciated the specific number and composition of parameters for which values are to be established is not significant to the principles underlying embodiments of the invention.

Embodiments of the invention seek to assist a user establish values for the plurality of parameters for the plurality of embryos. Each value is determined in turn. For the example implementation represented in FIG. 4 it is assumed the embryos are considered in turn while all the relevant parameters of interest are determined for each embryo (i.e. the relevant parameters of interest are first determined for one embryo, and then for another embryo, and so on). That is to say, there are two loops of iteration, and in accordance with the approach represented in FIG. 4 the processing iterates through the different embryos in an outer loop of iteration and through the parameters of interest for the respective embryos in an inner loop of iteration. However, the order in which the values are sought to be established is not significant. For example, in another implementation the parameters of interest may be established in turn for all embryos (i.e. one parameter of interest may be established for all embryos, and then another parameter of interest established for all embryos, and so on). It will be appreciated that values for parameters will only be established to the extent it is possible to do so. For example, if a particular embryo does not divide beyond the two-cell stage, it will not be possible to determine values for parameters associated with subsequent development events, such as t3, t4, MN4, and so on.

Thus, in step S3 of the processing represented in FIG. 4 an embryo is selected from the plurality of embryos (i.e. step S3 corresponds with the beginning of the outer loop of iteration). The embryo selected in step S3 may be referred to as the current embryo and is the embryo for which values for the parameters of interest will next be sought. As noted above there are assumed in this example to be nine embryos to analyse. The respective embryos (and their corresponding series of images) may be associated with identification numbers 1 to 9. This may be arbitrary, or may be based, for example, on an identifier associated with a location at which the particular embryo is/has been incubated, or any other scheme. In accordance with the approach represented in FIG. 4 the embryos are assumed to be automatically selected for analysis in turn according to their respective identification numbers. Thus in the first iteration through step S3 represented in FIG. 4 the embryo associated with identification number 1 is selected to be the current embryo. In another example a user may be invited to provide an indication of a particular embryo to be analysed next, and this may form the basis of the embryo selection in step S3. For example, a user may be provided with an opportunity to skip the analysis for an automatically selected embryo should they wish to.

In step S4 a parameter of interest is selected from the plurality of parameters of interest for which values are sought to be established (thus step S4 corresponds with the beginning of the inner loop of iteration). The parameter of interest selected in step S4 may be referred to as the current parameter of interest and is the parameter for which a value will next be sought for the current embryo. As noted above there are assumed in this example to be values for 12 parameters to seek to establish for each embryo. The respective parameters may be selected in an arbitrary order, but in this example the parameters are considered in a predefined order which is based, at least in part, on the order in which developmental stages associated with the respective parameters are expected to be apparent in the images comprising the timeseries for the respective embryo. In particular, it is assumed the parameters of interest are considered in an order: NOT2PN; t2; t3; t4; t5; t6; t7; t8; MN2; UNEVEN2; MN4; and UNEVEN4. This order is based on the ordering of the corresponding developmental stages only in part in as much as the parameters relating to cell division timings t2 to t8 are established in sequence, and then after this some characteristics relating to the morphology of the embryo at earlier stages are considered (e.g. MN2 and UNEVEN2). For the approach of FIG. 4 the parameters of interest may therefore be automatically selected for analysis in turn according to this predefined ordering. Thus, in the first iteration through step S4 represented in FIG. 4, the parameter NOT2PN is selected as the current parameter of interest. In another example a user may be invited to provide an indication of, or modify, a particular parameter of interest to be analysed next, and this may form the basis of the selection in step S4. For example, a user may be provided with an opportunity to skip a particular parameter.

In step S5 an image from the timeseries, which may be referred to as an initial image for the current embryo and current parameter of interest, is automatically selected. This initial image is presented on the display screen of the apparatus for viewing by a user in step S6. The initial image is intended to represent a point in the timeseries of images for the embryo which corresponds with the relevant development associated for the current parameter of interest. Significantly, the image which is presented to the user in step S6 is determined automatically. This relieves the user of the burden of navigating through the timeseries of images to seek to identify a point from which start determining a parameter of interest. There are various ways in which the initial image/timing can be predicted, and different ways may be used for different parameters of interest.

For example, in accordance with one approach the initial images may be selected based on a database representing typical timings for developmental events associated with various parameters of interest. The database may be based, for example, on previous experience/published data. For example, the database may indicate that whether or not two pro-nuclei are observed for the embryo might be most likely apparent at a time around $T_{PN}$. Based on this an appropriate initial image for assessing this characteristic may be selected as an image in the timeseries that is closest in time to $T_{PN}$. Similarly, the database may indicate that a value for t2 might typically be expected to fall in a range from $T_{t2LOW}$ to $T_{t2HIGH}$, and as such, an appropriate initial image for assessing a value for this parameter might be an image in the timeseries around $T_{t2LOW}$, or perhaps just before. Alternatively, a corresponding range could be based on the expected developmental timings for an embryo based on previous annotated development timings. For example, a predicted range for t5 ($T_{t5LOW}$ to $T_{t5HIGH}$) might be based on annotated values for one or more of t2, t3, or t4, for example by taking account of an expected additional time to t5 from an earlier developmental event.

In accordance with another approach the initial image selected for each parameter of interest may be determined from numerical processing of the images comprising the timeseries. For example, conventional image analysis techniques may be used to characterise an amount of change between successive pairs of images comprising the timeseries. An example plot of such an "activity" curve determined in accordance with conventional techniques is shown towards the bottom of FIG. 1. The times at which spikes occur in the activity curve represent times of relatively high morphological change, for example associated with cell division events. For example, referring to FIG. 1, there is a clear spike around the time t2, and also further spikes in activity around the times t3 and t4, and again spikes around the times t5. The locations of the spikes can be used to automatically select an initial image for a particular parameter of interest.

In general there are various different ways in which the images may be processed to determine appropriate initial images for display in association with any particular parameter of interest. For example, principles similar to those described in U.S. Pat. No. 7,672,369 B2 [1] and U.S. Pat. No. 7,963,906 B2 [2] may be used to automatically establish timings for particular cell development events, and then initial images to represent to a user for use in accordance with embodiments of the invention to assist the user establish a value for a parameter associated with the relevant developmental events may be determined from these timings. Furthermore, the specific method used may depend on the nature of the parameter of interest. For example, for parameters of interest corresponding with timings for cell division events, a method based on determining an embryo's morphological activity may be used (e.g. identifying times where there are relatively large differences in successive images). For other parameters, for example relating to the appearance of pro-nuclei, other methods may be used, for example specific timings may be defined for particular events, for example 16 to 18 hours post insemination for establishing NOT2PN. Other pre-defined timings can be used for determining other morphological grading characteristics (such as evenness, multinuclearity) as appropriate. Furthermore, initial images determined for some establishing values for some characteristics may be based on previously annotated events. For example, once t2 is annotated to indicate the time at which the embryo divides into two cells, this may be used to select an appropriate initial image to display to a user for establishing values for MN2 and EVEN2. For example, the first image following t2 may be selected as initial image for these characteristics. Thus in step S6 the user is automatically presented with an initial image that has been selected according to the current parameter of interest. For the first iteration through step S5 the current parameter of interest in this particular implementations is NOT2PN. Thus, in step S5 an initial image is selected which is predicted to show a development stage for the current embryo in which the user can establish a value for NOT2PN based on a conventional clinical assessment. As noted above, an initial image for establishing a value for NOT2PN may be determined by selecting whichever image is closest to (or immediately preceding) a pre-defined time, such as 16 hours post insemination.

FIG. 5 schematically shows a display component of a user interface which is displayed on the display screen 34 of the apparatus of FIG. 3 in accordance with an embodiment of the present invention. The display represents the display screen 34 at a stage corresponding to step S6 during the first iteration through the processing of FIG. 4, i.e. with the current embryo being embryo 1 and the current parameter of interest being NOT2PN. The display comprises various elements as now explained.

The main element is the currently-displayed embryo image.

To the right of the embryo image is an indication of the number of embryos comprising the current study. There are 24 numbered boxes under the heading "Embryo" and the first nine boxes (numbered 1 to 9) are shown with shading to indicate there are nine embryos comprising the study. Furthermore, box number 1 (corresponding to embryo 1) in this list of boxes is shown with different shading to indicate the currently displayed image is associated with embryo 1.

To the right of the boxes under the heading "Parameter" is an indication of the parameters of interest for the current study. There are 12 boxes under the heading "Parameter" and these are labelled according to the different parameters of interest (e.g. NOT2PN, t2, t3 . . . etc.). Furthermore, the parameter box labelled NOT2PN in this list of boxes is shown with different shading to indicate this is the current parameter of interest (i.e. the displayed image has been automatically selected with a view to assisting a user establish a value for this parameter of interest). To the right of the boxes indicating the parameters of interest for the current study are indications of any values that have already been established for these parameters.

To the left of the embryo image is a column of boxes indicating potential values that a user may select for the current parameter of interest. For the case of establishing a value for NOT2PN the potential values are) "0", "1", "2", "3", "4 or more", as indicated by the top five boxes to the left of the embryo image. Below these five boxes is a box labelled "NA" which a user may use to indicate no value is being established for the current parameter of interest and embryo.

At the bottom of this columns of boxes to the left of the embryo image are boxes labelled "Back(−)" and "Skip(+)" which a user may select to step backwards or forwards through the timeseries of images relative to a currently displayed image. For example, and as schematically indicated in step S7 in FIG. 4, if the user determines that the automatically selected image currently displayed (i.e. the initial image established in step S5) does not allow a value for the current parameter of interest to be established, the user may change to other images by stepping (scrolling) through the timeseries of images forwards and/or backwards relative to the initially selected image by selecting these navigation buttons using the mouse 40, or pressing corresponding "shortcut" keys, such as "−" and "+" keys, on the keyboard 38, or using some other user input device, such as a scroll wheel. The user may continue to scroll backwards and/or forwards around the automatically selected initial image until an image is found which is considered to allow the user to apply their clinical judgement in determining an appropriate value for the current parameter of interest.

In step S8 the user provides the apparatus with an indication of a value established for the current parameter of interest. This may also be referred to herein as an annotation indication. The annotation indication may comprise the user selecting one of the boxes indicating potential values for the current parameter using the mouse 40, or pressing a corresponding "shortcut" key.

In step S9 the apparatus 4 stores a record of the annotation indication (established value) for the current embryo and current parameter of interest. For example, this may be stored as a record in the RAM 28 or HDD 30 in accordance with conventional data storage techniques. Once an annotation indication for the current parameter of interest is received in step S9, processing proceeds to step S10 where it is determined whether or not there is another parameter to annotate for the current embryo. If it is determined there is another parameter, processing returns to step S4 where the next parameter is selected for annotation.

For the first iteration through step S10 in this particular example the current parameter of interest is NOT2PN and there are 11 more parameters of interest to establish for the current embryo (embryo 1). Accordingly, at this stage the processing follows the branch marked "yes" back to step S4 where the next parameter of interest for which a value to be established is selected, which in this example is t2. Steps S5 to S10 are then repeated with the current embryo remaining as embryo 1, but the parameter of interest now being t2.

Thus in step S6 of an iteration of the method represented in FIG. 4 in which the current parameter of interest is t2 the user is automatically presented with an initial image that has been selected in step S5 by taking account of the fact the current parameter of interest is t2. Thus, in step S5 of this iteration an initial image is selected which is predicted to show a development stage for the current embryo from which the user can establish a value for t2 based on a conventional clinical assessment. As noted above, there are various ways in which an initial image for t2 may be established. For example, in accordance with some implementations the initial image may be based on numerically processing the timeseries of images to identify where there are significant changes occurring between successive images. The extent of changes between images may be determined in accordance with conventional image processing techniques. Peak detection may then be applied to identify the first time in which there is a significant rearrangement in embryo morphology, and this may be deemed to in effect correspond to a predicted timing for t2. An initial image may then been selected based on this predicted timing. For example, the initial image may be whichever image is closest to the predicted timing, or the latest image before the predicted timing, or an image that precedes the predicted timing by a given amount (e.g. one hour).

FIG. 6 is similar to, and will be understood from, FIG. 5, but schematically shows what is displayed on the display screen 34 at a stage corresponding to step S6 during the iteration through the processing of FIG. 4 in which the current embryo is embryo 1 and the current parameter of interest is t2. The display comprises various elements which broadly correspond with the elements found in FIG. 5. However, there is a difference in how the user provides input to indicate an established value for t2. This reflects the fact t2 has a value corresponding to a timing (in effect a continuous variable) while NOT2PN has a value corresponding to a discrete number of potential values. Accordingly, whereas FIG. 5 shows a plurality of boxes corresponding to the plurality of discrete potential values for NOT2PN, the corresponding area of FIG. 6 comprises a single box labelled "t2(Enter)". Thus, a user starts from the initial image automatically determined in step S5 and navigates to an image which is considered to show the embryo at a stage corresponding to t2. This is performed in step S7 of the iteration in which the current parameter of interest is t2. Once this image is identified, in accordance with the user's clinical judgement, the user may simply select the "t2 (enter)" button to indicate the currently displayed image is at a time corresponding to the established value for t2. The user may select this button by clicking on it using a cursor driven by the mouse in the usual way, or may press a defined keyboard shortcut, which in this case is "Enter".

Thus, in step S8 the annotation indication from the user may simply comprise the user pressing an "Enter" button on the keyboard. In response to this, the processing proceeds to step S9 where a record for the established value for t2 is stored, and then on to step S10 where it is determined whether any further parameters are to be annotated for the current embryo.

Thus, processing proceeds to iterate through steps S4 to S10 until annotations have been established for all parameters of interest for the first embryo.

FIGS. 7 to 14 are similar to, and will be understood from, FIGS. 5 and 6, but schematically show what is displayed on the display screen 34 at stages corresponding to step S6 during various iterations through the processing of FIG. 4 in which the current embryo is embryo 1 for various parameters of interest. For each figure the current parameter of interest is shown by lighter shading in the column headed "Parameter", and for each figure, the values which the corresponding parameter can adopt may be input using the buttons to the left of the embryo image as discussed above for FIGS. 5 and 6. It may be noted for this particular embryo the timings for t3 and t4 are determined to be simultaneous within the resolution of the timeseries, and as such may be established from a single image (FIG. 7).

Once the process has iterated through steps S4 to S10 to establish values for all parameters of interest for embryo 1, processing follows the branch marked "No" from step S10 to step S11. Here it is determined whether there are any other embryos to annotate. If so, processing returns to step S3 where the next embryo for annotation is selected, and then on to step S4 for a further iteration around steps S4 to step S10 for all parameters of interest for the newly-selected current embryo. In the example represented in FIG. 4 there will be nine iterations through the outer loop between steps S3 and S11, after which values will have been established, so far as possible, for all parameters of interest and embryos.

Once all embryos have been considered and it is determined in step S11 there are no further embryos to annotate processing proceeds to step S12.

In step S12 an indication of the values for the various parameters that have been established is output. This may be in the form of a data file to be stored for further use, or may be in the form of a display presented to a user.

FIG. 16 represents one such display where the established values are indicated in a tabular format with values associated with each embryo being represented in rows against the relevant embryo identification number (listed in the column headed "well"). The values represented in the table of FIG. 16 are those which can subsequently be used in accordance with any established techniques for determining the development potential of an embryo using such values. In an implementation in which the method further comprises determining a measure of embryo quality from the established values (which itself may be performed in accordance with any known techniques), the tabular representation in FIG. 16 may also include a column indicating this measure. This is schematically shown in FIG. 16 under the heading "current score", although for this particular representation, the scores have not yet been determined.

It will be seen in FIG. 16 that it is not possible to establish values for all parameters of interest. For example, for some of the embryos (embryos numbered 3, 5, and 6) there have been no parameters established beyond NOT2PN. This is because these embryos are identified with values of OPN (i.e. zero PN) for the parameter NOT2PN. This indicate these embryos were not viable and did not develop further, and hence no further values have been established for the other parameters. In this regard, if during the processing represented in FIG. 4 it is determined that an embryo is not viable based on an established value for one of the parameters (e.g. a value of OPN for NOT2PN), the processing may be configured to skip directly to the next embryo without attempting to establish values for other parameters of interest. Similarly, it can be seen from FIG. 16 that it was not possible to establish values for various parameters for embryo 4, and this may reflect the fact that embryo 4 did not develop beyond t4. In some examples it may be decided not to attempt to establish values for specific embryos before entering into the process represented in FIG. 4, and these embryos will then be skipped during the process represented in FIG. 4.

A table such as that represented in FIG. 16 may be viewed at the completion of annotation for the study, or may be presented to a user, for example on request by the user, at any stage during the processing represented in FIG. 4. In this case the parameters for which values have already been established may be presented to the user. For the parameters that have not yet been established, the user may be instead presented with predicted values. For example for the cell division timings, the user may be presented with predicted timings corresponding to those that are established in step S5 for the relevant parameters. If the user is presented with both established and predicted values, they may be displayed differently. For example, the values that have already been positively established may be presented in black, while the values that are predicted may be greyed out.

Figure 17:
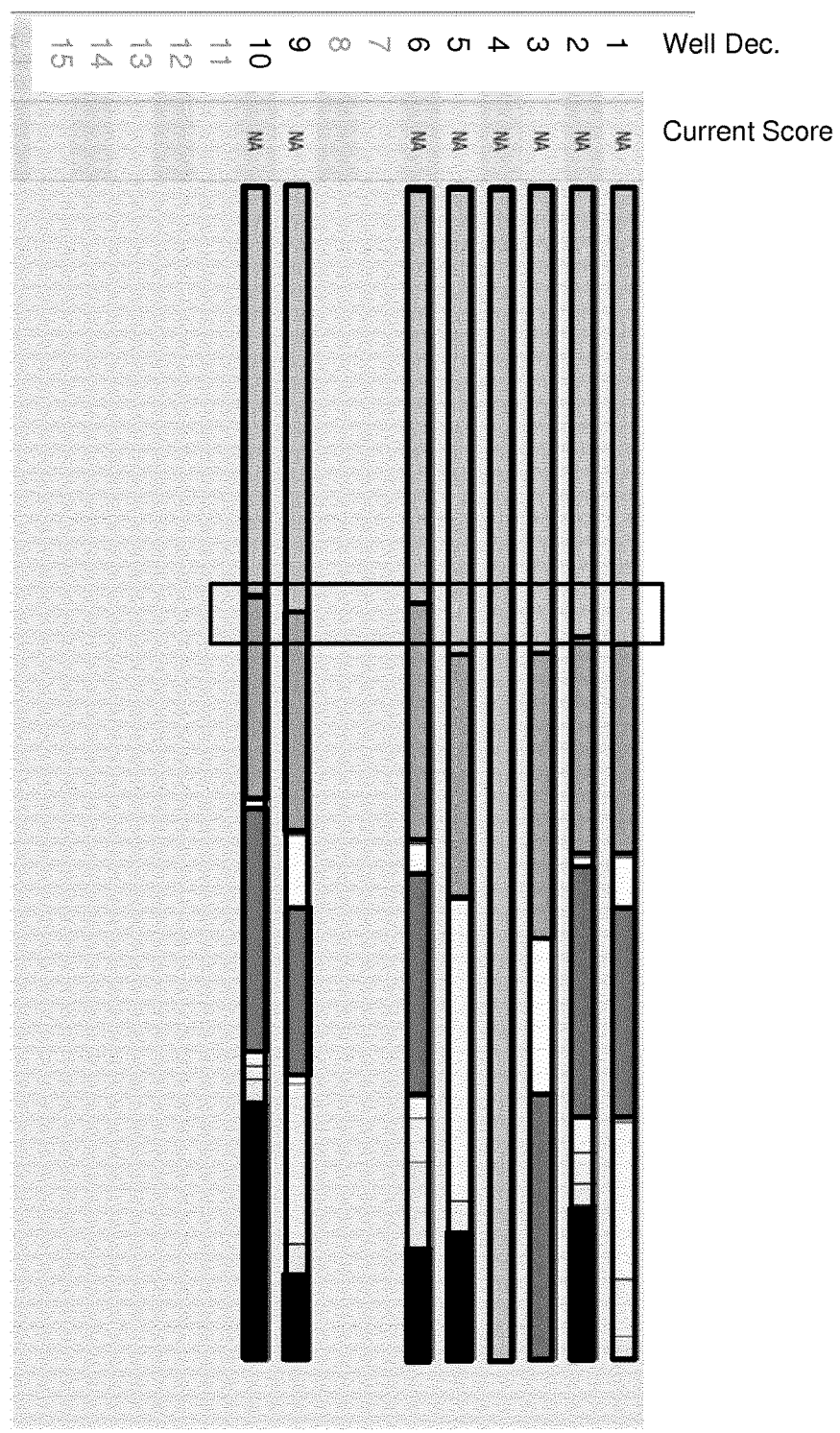
FIG. 17 schematically shows a display of values for parameters relating to the development of one or more embryos in accordance with another embodiment of the invention.

In addition to presenting information regarding the established values in a tabular form, the information may be presented in a graphical form. An example of this is represented in FIG. 17. In this case data are shown for eight embryos labelled 1 to 6, 9 and 10 (i.e. this data is based on a different study from the data represented in FIG. 16). For each embryo a time bar is presented with periods between different cleavage events being represented by different coloured bands (i.e. the coloured bands represent the durations of the periods during which the embryo comprises different numbers of cells). This provides a ready mechanism for a user to appreciate the relative durations of the relative development phases for the different embryos in a study. Furthermore, the display may be overlaid with markings, such as the dark rectangle seen in FIG. 17, to provide an indication of acceptable or preferred values for various parameters. This graphical approach can give a user an immediate feeling for which embryos have developed well and which embryos have developed less well. For example, a high degree of synchronicity in cell divisions within the same generation is generally an indicator of a good-quality embryo. In FIG. 17 the period spent as a three cell embryo is shown in the lightest shading. A small size for this region, for example for embryo 10, is an indicator of a potentially better quality embryo that a larger size, for example for embryo 3. The representation presented in FIG. 17 may in some examples be provided with time-line markings.

Thus, approaches of the kind described above and as represented in FIG. 4 provide schemes for assisting a user perform the task of establishing values for a plurality of parameters of interest from time-lapse images embryos. Approaches in accordance with embodiments of the invention had been found to be faster than existing techniques. This is because a user is automatically presented with an initial image which is selected according to the parameter to be annotated, thereby relieving the user of the task of navigating through the entire series of images to identify relevant developmental events "from scratch". Furthermore, because at each stage the user is presented with an image which is associated with establishing a value for a particular parameter of interest, the user can simply provide an indication of the value, without having to provide an indication of what the parameter is. This means, for example, a user can simply provide the same input (e.g. pressing an "enter" button) when a currently-displayed image is considered to properly represent a particular timing to be allocated regardless of what the corresponding parameter is. Furthermore, in response to providing the annotation indication, the user may be automatically presented with a new image to help him with annotating the next parameter of interest. Overall, this approach has been found to provide a faster and more intuitive approach than existing techniques.

It will be appreciated the above-described example embodiments of the invention may be modified in various ways in accordance with other example embodiments of the invention.

For example, the specific ordering of the steps performed in FIG. 4 may be different in different implementations. For example, rather than include step S5 in the iterative process, it may be performed once to establish appropriate initial images for each parameter of interest. That is to say, a step correspond to step S5 but which determines initial images for all promise of interest may be performed between steps S3 and S4, for example.

Thus there has been described methods and apparatus for helping a user establish values (e.g. timings) for a plurality of parameters of interest (e.g. cell divisions) relating to the development of an embryo from a series of images of the embryo. For each parameter of interest an image is selected for display to a user seeking to establish a value for the parameter of interest. For example, the selected image may be an image predicted to be an image reflecting the value for the parameter of interest. For example, the selected image may be based on a calculated timing for a particular developmental event. The timing may be calculated from a numerical analysis of the images or maybe predetermined. If the user is unable to determine a value for the parameter of interest from the selected image, the user may scroll through neighbouring images until the user can determine a value for the parameter of interest. A value for the proud of interest may then be established in response to user input, for example a user providing an indication that a timing associated with a currently displayed image from the series of images should be taken to be the value of the parameter of interest. The different parameters of interest may be established in an iterative manner in which an initial image for display to a user is selected for each parameter of interest based on the parameter of interest.

Further particular and preferred aspects of the present invention are set out in the accompanying independent and dependent claims. It will be appreciated that features of the dependent claims may be combined with features of the independent claims in combinations other than those explicitly set out in the claims.

REFERENCES

[1] U.S. Pat. No. 7,672,369 B2
[2] U.S. Pat. No. 7,963,906 B2

What is claimed is:

1. A method for helping a user establish values for a plurality of parameters of interest relating to the development of at least one embryo from a series of images of the at least one embryo at different times during development, the method comprising
   providing stored computerized instructions that execute the following steps:
   (a) selecting a current parameter of interest from among the plurality of parameters of interest;
   (b) automatically selecting an image from within the series of images to display to a user for use in establishing a value for the current parameter of interest, wherein the image is selected according to a predefined association between series of images and the current parameter of interest;
   (c) displaying the selected image to the user on a display;
   (d) changing the image displayed on the display to another image from the series of images in response to user input;
   (e) establishing a value for the current parameter of interest in response to user input received through one or more user input devices; and
   (f) selecting another parameter of interest as the current parameter of interest, and repeating steps (b) to (e).

2. The method of claim 1, wherein repeating steps (b) to (e) in step (f) comprises also repeating step (f) until values for all parameters of interest have been established.

3. The method of claim 1, wherein the image is automatically selected in step (b) based on an analysis of the series of images.

4. The method of claim 3, wherein the analysis of the series of images comprises determining an indication of an amount of change between images comprising the series of images.

5. The method of claim 1, wherein the predefined association is based on comparing predefined timings associated with the respective parameters of interest with timings associated with the respective images.

6. The method of claim 1, further comprising helping a user establish values for a plurality of parameters of interest relating to the development of a further embryo from a series of images of the further embryo, the method comprising:
   (h) selecting a current parameter of interest from among the plurality of parameters of interest for the further embryo;
   (i) automatically selecting an image from within the series of images of the further embryo to display to a user for use in establishing a value for the current parameter of interest, wherein the image is selected according to the current parameter of interest;

(j) displaying the selected image to the user on a display;

(k) changing the image displayed on the display to another image from the series of images in response to user input;

(l) establishing a value for the current parameter of interest for the further embryo in response to user input; and (m) selecting another parameter of interest as the current parameter of interest, and repeating steps (i) to (m).

7. The method of claim 6, wherein values for the different parameters of interest for the different embryos are established in turn by:

establishing different parameters of interest for one of the embryos and then establishing the different parameters of interest for the other of the embryos; or by establishing a parameter of interest for the different embryos and then establishing another parameter of interest for the different embryos.

8. The method of claim 1, wherein the parameters of interest comprise times for developmental events for the at least one embryo.

9. The method of claim 8, wherein the image is automatically selected in step (b) based on a predicted timing for a developmental event associated with the current parameter of interest.

10. The method of claim 1, wherein the values for the parameters of interest are user-classifications of embryo characteristics.

11. The method of claim 10, wherein the image is automatically selected in step (b) based on a predicted timing for an image in which the embryo characteristic associated with the current parameter of interest is predicted to be apparent.

12. The method of claim 1, wherein selecting a current parameter of interest in step (a) and/or selecting another parameter of interest in step (f) is based on user input.

13. The method of claim 1, wherein selecting a current parameter of interest in step (a) and/or selecting another parameter of interest in step (f) is performed automatically by selecting parameters of interest in accordance with a predefined sequence.

14. The method of claim 1, wherein step (f) is automatically performed in response to the user input of step (e).

15. The method of claim 1, wherein a value for the current parameter of interest is determined according to a timing associated with an image from the series of images which is displayed on the display when the user input is received in step (e).

16. The method of claim 1, further comprising displaying a representation of the values for the plurality of parameters of interest that have been established.

17. The method of claim 16, wherein the representation of the values for the plurality of parameters of interest that have been established is comprises a tabular representation or a graphical representation of the values for the plurality of parameters of interest that have been established.

18. The method of claim 16, further comprising displaying a representation of predicted values for at least some of the plurality of parameters of interest that have not been established.

19. The method of claim 18, wherein the values for the plurality of parameters of interest that have been established and the predicted values for the plurality of parameters of interest that have not been established are represented differently.

20. The method of claim 1, further comprising determining a development potential for the at least one embryo from one or more of the values established for the plurality of parameters of interest.

21. The method of claim 1, wherein the current parameter of interest selected in step (a) and the another parameter of interest selected in step (f) are associated with different embryos or are different parameters of interest associated with the same embryo.

22. A non-transitory computer program product bearing machine readable instructions for carrying out the method of claim 1.

23. An apparatus loaded with and operable to execute machine readable instructions for carrying out the method of claim 1.

24. An apparatus for helping a user establish values for a plurality of parameters of interest relating to the development of at least one embryo from a series of images of the at least one embryo at different times during development, the apparatus comprising a processor element and a user interface element comprising a display and one or more user input devices, and wherein the processor element is configured to cause the apparatus to perform the following steps:

(a) select a current parameter of interest from among the plurality of parameters of interest;

(b) select an image from within the series of images to display to a user for use in establishing a value for the current parameter of interest, wherein the image is selected automatically according to a predefined association between series of images and the current parameter of interest;

(c) display the selected image to the user on the display;

(d) change the image displayed on the display to another image from the series of images in response to user input received through the one or more user input devices;

(e) establish a value for the current parameter of interest in response to user input received through the one or more user input devices; and (f) select another parameter of interest as the current parameter of interest, and repeating steps (b) to (e).

* * * * *